United States Patent
Laudon et al.

(10) Patent No.: US 7,635,710 B2
(45) Date of Patent: Dec. 22, 2009

(54) PYRONE-INDOLE DERIVATIVES AND PROCESS FOR THEIR PREPARATION

(75) Inventors: Moshe Laudon, Kfar Saba (IL); Tal Peleg-Shulman, Tel Aviv (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 11/705,030

(22) Filed: Feb. 12, 2007

(65) Prior Publication Data

US 2008/0027121 A1 Jan. 31, 2008

Related U.S. Application Data

(60) Provisional application No. 60/773,322, filed on Feb. 15, 2006.

(51) Int. Cl.
*A61K 31/404* (2006.01)
(52) U.S. Cl. ............ 514/414; 514/415; 548/467
(58) Field of Classification Search ........... 514/414, 514/415; 548/467
See application file for complete search history.

(56) References Cited

U.S. PATENT DOCUMENTS 5,789,440 A * 8/1998 Ellsworth et al. ........... 514/460

2007/0232663 A1 * 10/2007 Pirrung ................. 514/337

FOREIGN PATENT DOCUMENTS

| CA | 02222471 | * | 10/1997 |
| EP | 0272228 A2 | | 6/1988 |
| WO | 9207829 A1 | | 5/1992 |
| WO | 0072815 A1 | | 12/2000 |
| WO | WO 01/79187 A2 | * | 10/2001 |
| WO | 2006002125 A1 | | 1/2006 |

OTHER PUBLICATIONS

STN search-Chemical Abstracts. Registry No. 732999-96-1, entered Aug. 26, 2004, supplier: Enamine.*
Maiti, Bhim C., et al., "Reaction of dehydroacetic acid with aliphatic, aromatic and heterocyclic amines," Indian Journal of Chemistry, 37B: 710-712 (Jul. 1998).
Novák, Lajos, et al., "Heterocyclic Analogs of Mevinolin," Liebigs Annalen Der Chemie, No. 10, 1877-1883 (1995).
Steinhilber, Dieter, et al., "Melatonin receptor ligands," Expert Opinion on Therapeutic Patents, 9(3):281-290 (1999).
WIPO, International Search Report and Written Opinion of the Examining Authority for PCT/IB2007/000330 dated Aug. 13, 2007.

* cited by examiner

*Primary Examiner*—Kamal A Saeed
*Assistant Examiner*—Valerie Rodriguez-Garcia
(74) *Attorney, Agent, or Firm*—Rothwell, Figg, Ernst & Manbeck

(57) ABSTRACT

The present invention relates to novel pyrone-indole derivatives, pharmaceutical formulations containing them, and use of the compounds in the manufacture of Medicaments for treating or preventing various diseases.

56 Claims, No Drawings

PYRONE-INDOLE DERIVATIVES AND PROCESS FOR THEIR PREPARATION

This application claims priority from U.S. patent application 60/773,322, filed Feb. 15, 2006. This application is incorporated herein by reference.

BACKGROUND OF THE INVENTION

The alpha and gamma-pyrones are classes of compounds shown to be linked to several behavioral and pharmacological characteristics including sedative, anxiolytic, neuroprotective and antioxidative effects. Specifically, a gamma-pyrone derivative called maltol has been isolated from passion flower and shown to cause central nervous system (CNS) sedation and a reduction in caffeine-induced agitation and spontaneous motility in animals; these effects are mediated via activation of gamma-aminobutyric acid (GABA) receptors (Soulimani et al., J. Ethnopharmacology 57:11, 1997; Dhawan et al., J. Ethnopharmacology 78: 165-70, 2001). Other members of this family, the gamma-pyrones comenic, meconic and chelidonic acids have been shown to exert sedative effects via interaction with opiod receptors (U.S. Patent Application No. 2003/0181516).

The $GABA_a$ receptor superfamily represents one of the classes of receptors through which the major inhibitory neurotransmitter, GABA, acts. Widely, although unequally, distributed through the mammalian brain, these receptors, and in particular a complex of proteins called the $GABA_a$ receptor, cause alterations in chloride conductance and membrane polarization (Mehta and Ticku, Brain Res. Brain Rev. 29:196-217, 1999).

Benzodiazepine drugs exert their hypnotic, analgesic and anxiolytic actions by interacting with the benzodiazepine binding sites at the $GABA_a$ receptor. In addition to the benzodiazepine-binding site, the $GABA_a$ receptor contains several distinct sites of interaction with other classes of drugs that modulate GABAergic activities, including nonbenzodiazepine hypnotics (e.g. zolpidem, zaleplon, indiplon, zopiclone) (Sanger, CNS Drugs 18 (Suppl. 1):9-15, 2004), steroids, pictrotoxin and barbiturates. The benzodiazepine and non-benzodiazepine binding sites in the GABAa receptor complex do not overlap with the GABA or any of the other drug binding sites (see, e.g., Cooper, et al., The Biochemical Basis of Neuropharmacology, 6th ed., pp. 145-148, Oxford University Press, New York, 1991). Electrophysiological studies indicate that the major action of the benzodiazepines and nonbenzodiazepines is enhancement of GABAergic inhibition of neuronal excitability. This is due to potentiation of the GABA-induced chloride influx into the cells and subsequently membrane hyperpolarization. The clinically important alloseteric modulation of the GABA receptors by benzodiazepines and non-benzodiazepines has been an area of intense pharmacological discovery in recent years. Agonists that act at the benzodiazepine site are known to exhibit anxiolytic, sedative and hypnotic effects, while compounds that act as inverse agonists at this site elicit anxiogenic, cognition enhancing, and proconvulsant effects (Dawson et al., CNS Spectr. 10:21-7, 2005).

The major disorders for which $GABA_a$ receptors represent important therapeutic targets include anxiety disorders, cognitive disorders, epilepsies, mood disorders, schizophrenia, pain and sleep disorders. GABA receptor modulators are known to play an important role in sleep and positive allosteric modulators of $GABA_a$ receptors are widely used to promote and maintain sleep in a variety of primary and secondary sleep disorders (Sanger, CNS Drugs, 18 (Suppl. 1):9-15, 2004).

While benzodiazepines have a long history of pharmaceutical use as anxiolytics, these compounds often exhibit a number of unwanted side effects. These may include cognitive impairment, sedation, ataxia, potentiation of ethanol effects, increased risk of falls and a tendency for tolerance and drug dependence. An important aspect of these activities is the residual daytime effect resulting in impairment of daytime vigilance. Therefore new GABA receptor modulators with less untoward side effects are sought.

Indole compounds, specifically those related to serotonin (5-hydroxytryptamine; 5-HT) and melatonin (N-acetyl-5-methoxy-tryptamine) have profound CNS effects and thus impinge on sleep, wakefulness, appetite and mood. There are an extensive number of clinically relevant areas where the involvement of the melatonin system has been demonstrated (Bubenik et al., Biol. Signals Recept. 7:195-219, 1998). These include regulation of core body temperature (Strassman et al., J. Appl. Physiol. 71:2178-2182, 1991; Krauchi et al., J. Appl. Physiol. 83:134-9, 1997), immune responses, (Maestroni and Conti, J. Neuroimmun. 28:167-176 1990; Fraschini et al., Acta Oncol. 29:775-776, 1990; Guerrero and Reiter, Endocr. Res. 18:91-113, 1992), pubertal development, ovulation, seasonal reproduction, retroperitoneal and epididymal fat, as well as plasma insulin, leptin, growth hormone and ghrelin levels (Rasmussen et al., Endocrinology 140: 1009-12, 1999; Cramer et al., Arzeneim-Forsch 26:1076-1078, 1976; Wright et al., Clin. Endocrinol. 24:375-382, 1986, Paccotti et al., Chronobiologia 15:279-288, 1988; Valcavi et al., Clin. Endocrinol. 39:139-199, 1993; Mustonen et al., Endocrine 16:43-6, 2001), cortisol rhythms, ocular pressure (Sampes et al. Curr. Eye Res. 7:649-653, 1988; Rhode et al., Ophthalmic Res. 25:10-15, 1993), blood pressure (Scheer et al., Hypertension 43-192-7, 2004), glucose metabolism, ghrelin, leptin and body fat mass, vasopressin and urine excretion (Song et al., FASEB J. 11:93-100, 1997; Yasin et al., Brain Res. Bull. 39:1-5, 1997). In some instances, psychiatric disorders may have underlying chronobiological etiologies (e.g. seasonal effective disorder) and are definite candidates for melatonin therapy (Miller, Altem. Med. Rev. 10:5-13, 2005). Melatonin also acts as a free radical scavenger and anti-oxidant (Pooggeler et al., J. Pineal Res. 14:151-168, 1993).

There is very strong evidence that melatonin specifically regulates sleep and wakefulness in humans. Melatonin has been administered to re-synchronize circadian rhythms that are out of phase with the local photoperiodical cycle. For example, sleep/wake disorders caused by rapid crossing of time zones (et lag), delayed sleep phase syndrome (DSPS) patients, shift work and total blindness, can be treated with melatonin or melatonin analogs (see U.S. Pat. Nos. 4,600,723 and 4,666,086 of Short et al. and U.S. Pat. No. 5,242,941 of Lewy et al.). In addition, melatonin has direct sedative/hypnotic properties in both normal and insomniac human subjects (e.g., Luboshizsky et al., Sleep Med. Rev. 2:191-202, 1998; U.S. Pat. No. 5,403,851 of D'Orlando et al.). Sleep disorders in the elderly have been shown to respond to melatonin treatment (Garfinkel et al., Lancet 346:541-543, 1995; Pandi-Perumal et al., Exp. Gerontol. 40:911-25, 2005; U.S. Pat. No. 5,498,423 of Zisapel). Melatonin and its analogs reduce latency to sleep onset in patients with insomnia (Roth et al., Sleep, 28:303-7, 2005, Zhdanova et al., Clin. Pharmacol. Ther. 57:552-8, 1995) or depression (Papp et al., Neuropsychopharmacology 28:694-703, 2003) and particularly enhance the restorative value of sleep in insomnia patients, resulting in enhanced daytime vigilance (Zisapel, PCT Patent application No. WO 03/015690).

There is a wide spectrum of symptomatic responses to melatonin treatments in different disorders. These include anxiety (Loiseu et al., Eur. Neuropsychopharmcol. 2005), seizures (Munoz-Hoyos et al., J. Child. Neurol. 13:501-9, 1998), pain (Ray et al., Indian J. Med. Sci. 58:122-30, 2004), cluster headache and migraine (Peres, Cephalalgia 25:403-11, 2005), depression, mania and schizophrenia (see Dobocovich "Antidepressant Agents", U.S. Pat. No. 5,093,352; Shamir et al., J. Clin. Psychopharmacol. 20:691-4, 2000), glaucoma, aging, stress (Armstrong and Redman, Med. Hypotheses 34:300-309, 1991; Reiter, Bioassays 14: 169-175, 1992), hypertension (Scheer et al, Hypertension 43:192-7, 2004, Zisapel, U.S. patent application Ser. No. 10/169, 467), drug withdrawal syndromes (Zisapel, U.S. Pat. No. 6,469,044), osteoporosis (Cardinali et al., J. Pineal Res. 34:81-7, 2003), various cancers (Gonzalez et al., Melanoma Res. 1:237-243, 1991; Lissoni et al., Eur. J. Cancer 29A:185-189, 1993; Blask et al., Endocrine 27:179-88, 2005; U.S. Pat. No. 5,196,435 of Clemens et al. and U.S. Pat. No. 5,272,141 of Fraschini et al.), benign tumors and proliferative diseases such as Benign Prostatic Hyperplasia (BPH) (U.S. Pat. No. 5,750,557 and European Patent No. EP 0565296B of Zisapel), psoriasis, contraception and fertility, precocious puberty, premenstrual syndrome and hyperprolactinemia (Pevre et al., J. Clin. Endocrinol. Metab. 47:1383-1388, 1978; Purry et al., Am. J. Psychiatry 144:762-766, 1987; Waldhauser et al., Clin. Endocrinol. Metab. 73:793-796, 1991; Bispink et al., J. Pineal Res. 8:97-106, 1990; Cagnacci et al., J. Clin. Endocrinol. Metab. 73:210-220, 1991; Voordouw et al., J. Clin. Endocrinol. Metab. 74:10-108, 1992; see U.S. Pat. Nos. 4,855,305 and 4,945,103 of Cohen et al. and U.S. Pat. No. 5,272,141 of Fraschini et al.).

Melatonin is beneficial for the treatment and prevention of neurodegenerative disorders (Skene et al., Brain Rev. 528: 170-174, 1990; Feng et al., J. Pineal Res. 37:129-36, 2004), ischemic stroke (Cho et al., Brain Research 755:335-338, 1997; Reiter et al., Exp. Biol. Med. 230:104-17, 2005), Alzheimer's disease (Pappola et al., J. Neurosci. 17:1683-90, 1997; Feng and Zhang, Free Radic. Biol. Med. 37:1790-801, 2004) and sudden infant death syndrome (SIDS) (U.S. Pat. No. 5,500,225 of Laudon et al.).

Three melatonin receptor subtypes have been identified so far: MT-1, MT-2 and dihydronicotinamide riboside-quinone reductase 2 that is sometimes referred to as MT-3 or ML2 melatonin receptors (Dubocovich et al., IUPHAR media, London, UK, 187-93, 1998; Maillet et al., FEBS Lett. 3:578-116-20, 2004). MT-1 is localized in the CNS and in peripheral organs such as the kidneys and the urogenital tract, while MT-2 is located mainly in the central nervous system. There are no physiological activities ascribed to the MT-3 (ML2) sites. In addition, melatonin interacts with intracellular proteins such as calmodulin (Anton-Tay et al., J. Pineal Res. 24:35-42, 1998) and tubulin-associated proteins (Cardinali et al., J. Pineal Res. 23:32-9, 1997). Retention patterns of radioactive-melatonin injected into rats demonstrate melatonin accumulation in the brain, pituitary, lung, heart, gonads and accessory sex organs (Withyachumnamkul et al., Life Sci. 12:1575-65, 1986).

It is clear that there exists a broad range of therapeutic uses for melatonin and its analogs. Accordingly, it is of continuing interest to identify novel compounds that interact with the melatoninergic system as potential therapeutic agents (Zlotos, Arch. Pharm. Chem. Life Sci. 338:229-247, 2005). These compounds may offer longer duration, selective localization and greater efficacy to those of melatonin.

Serotonin (5-HT) is now known to modulate numerous physiologic and behavioral systems that explain the many 5-HT based drugs used as treatments in very different clinical conditions. There are extensive therapeutics directed at increasing or decreasing 5-HT function at selected sites, in widely different clinical conditions. Probes of 5-HT turnover in CNS and peripheral tissue have demonstrated alterations in 5-HT metabolism to be associated with a wide number of clinical conditions, and many drugs, such as antidepressants, antipsychotics, and anxiolytics, have been shown to alter 5-HT function in several disorders. The development and widespread clinical use of selective 5-HT reuptake inhibitors (SSRI), and the preclinical delineation of the multiple 5-HT receptor subtypes and their couplings to intracellular messenger systems and the development of drugs selectively acting on these systems, have catalyzed an explosion of new research information in this field. It is now clear that the 5-HT systems are extremely diverse, and that they are involved in a multitude of physiologic and behavioral processes. In contrast, the development of specific 5-HT receptor agonists and antagonists have led to more specific targeted therapeutic interventions such as the use of the 5-HT agonist, sumatriptin, in migraine and cluster headache, and the $5-HT_3$ antagonist, ondansetron in the control of nausea and emesis.

There are an extensive number of clinically relevant areas in which the involvement of the 5-HT system has been demonstrated. These include mood regulation, fear and anxiety, learning and memory, cognitive control, appetite and eating regulation, sleep, sexual function, impulse control, developmental behavioral regulation, aging and neurodegeneration, motivation and reward, pain sensitivity, emesis, myoclonus, neuroendocrine regulation, circadian rhythm regulation, stress response and carcinoid syndrome.

There is a wide spectrum of symptomatic responses to selective serotonin reuptake inhibitor (SSRI) treatments in different disorders. The increased availability of a number of SSRI's for clinical use has led to treatment trials in a wide variety of different clinical conditions. Placebo controlled studies have demonstrated positive results of SSRI treatment in: depression, obsessive-compulsive disorder (OCD), panic disorder, premenstrual syndrome, bulimia nervosa, autistic disorder, diabetic neuropathy, and diabetic obesity. The wide spectrum of different clinical conditions that have been reported to demonstrate a symptomatic response following SSRI treatment includes major depression, depression secondary to medical condition, post stroke depression, dysthymia, seasonal affective disorder, OCD, panic disorder, social phobia, borderline personality disorder, depersonalization syndrome, body dysmorphic syndrome, premenstrual syndrome, postpartum disorders, bulimia nervosa, post traumatic stress disorder, autistic disorder, attention deficit, hyperactivity disorder, Tourette's syndrome, trichotillomania, onychophagia, Prader-Willi syndrome, paraphillias and sexual addictions, premature ejaculation, migraine prophylaxis, diabetic neuropathy, pain syndromes, obesity, weight gain in smokers, alcoholism, emotional liability following brain injury, sleep paralysis, pathologic jealousy, chronic schizophrenia, self-injurious behavior, arthritis, Raynaud's phenomenon, fibromyalgia, chronic fatigue syndrome, irritable bowel syndrome, upright tilt syncope, intention myoclonus and neuroendocrine regulation.

The preclinical data on 5-HT indicate that the 5-HT systems are predominantly modulatory and that most 5-HT effects interact with the ongoing status of the other involved neurotransmitter systems. The neuroanatomy of the 5-HT system suggests that up to 60% or more of 5-HT released may not be at synapses. Thus, 5-HT effects would not be expected to be highly anatomically localized or demonstrate the properties associated with systems that more directly mediate neurotransmission. The modulatory nature of the 5-HT systems can be seen at the clinical level through interactions with other neurotransmitter systems. In behaving animals, the activity of brain serotonergic neurons is closely tied to the sleepwake-arousal cycle: highest firing rate during active waking or arousal, intermediate level of discharge during quiescent states and slow wave sleep, and virtual silence during rapid-eye movement sleep. Some SSRI compounds are associated with untoward weight loss or excessive weight gain, insomnia and sexual dysfunction.

The widespread involvement of the 5-HT systems in modulating the physiologic functions of a large number of different and important biological systems, coupled with the rapid progress of the molecular biological approach in discovering new 5-HT receptor subtypes, should foster increased research activity directed at the development of clinically applicable 5-HT modulators that can be endowed with other pharmacological properties in order to optimize the parameters of drug use for the clinical effect.

Novel compounds related to melatonin or serotonin and pyrones, but with pharmacological or pharmacokinetic profiles different from these molecules, are likely to be important new pharmaceuticals. For examples, see U.S. Pat. No. 5,403, 851, which discloses the use of substituted tryptamines, phenylalkylamines and related compounds, in order to treat a number of pharmaceutical indications including sleep disorders, endocrine indications, immune-system disorders etc. PCT Patent Application No. WO 87/00432 describes compositions for treating or preventing psoriasis that contain melatonin or related compounds. U.S. Pat. No. 5,122,535 discloses the production of melatonin and analogs thereof for various therapeutic purposes, including the administration of melatonin in combination with an azidothymidine for the treatment of AIDS. Melatonin analogs based on the bioisosteric properties of the naphthalenic ring and the indole ring have been disclosed in J. Med. Chem. 1992, 35: 1484-1485, EP 662471 A2 950712 of Depreux et al., WO 9529173 A1 951102 of Ladlow et al., U.S. Pat. No. 5,151,446 of Horn et al., U.S. Pat. No. 5,194,614 of Adrieux et al. and U.S. Pat. No. 5,276,051 of Lesieur et al. Melatonin and its analogs may potentiate the effects of GABA receptor modulators (Zisapel, U.S. Patent application No. US20055175692, Zisapel, U.S. Pat. No. 6,469,044).

Insulin resistance and non-insulin-dependent diabetes are prevalent in up to 35% of the population depending upon the age and nature of the subset. In the United States alone, 16 million people have type 2 diabetes and 13 million have impaired glucose tolerance. In fact, type 2 diabetes has reached epidemic proportions worldwide. By 2025, an estimated 300 million people will have diabetes, most of whom will inhabit China, India, and the United States. Because of an aging and increasingly sedentary, obese population with changing, unhealthy diets, insulin resistance is also increasing alarmingly (it is already two to three times more prevalent than type 2 diabetes).

Insulin resistance usually occurs early in the development of type 2 diabetes. An altered balance in the autonomic nervous system and in certain endocrine and inflammatory pathways might contribute to the development of insulin resistance. In diabetes, hyperglycemia further aggravates insulin resistance as well as beta cell dysfunction but the mechanisms causing this phenomenon, i.e. glucotoxicity, are not fully understood. Insulin resistance can be demonstrated in healthy first-degree relatives of type 2 diabetes patients who also have a high risk of developing type 2 diabetes.

The fasting hyperglycemia of type 2 diabetes exists in the presence of hyperinsulinemia; this reflects the presence of insulin resistance in the liver with resultant glycogenolysis and gluconeogenesis. In addition to the impaired insulin suppression of hepatic glucose production, a decrease of insulin-mediated glucose uptake by muscle cells contributes (about 50%) to the resultant hyperglycemia.

Glucose tolerance declines with age because of: 1) increased cell receptor resistance to insulin; 2) intracellular post receptor disturbances and 3) diminished pancreatic islet β-cell sensitivity to insulin and glucose. Insulin resistance, with secondary hyperinsulinemia and/or hyperglycemia, contributes to many disorders associated with aging, i.e., hypertension, obesity, atherosclerosis, lipid abnormalities, coagulopathies and chronic metabolic-perturbations including type 2 diabetes. Insulin is one of the most important anabolic hormones in the body and it is critical for the control of carbohydrate, lipid and protein metabolism. Insulin is secreted from beta cells in the endocrine pancreas. It acts by binding to the transmembrane insulin receptor in the target cells, and this activates the tyrosine kinase domain in the intracellular part of the receptor leading to phosphorylation of insulin receptor substrates (IRS). This starts a cascade of signaling reactions in the cell leading to metabolic effects. The main target tissues of insulin's metabolic action are muscle, liver and adipose tissue. Insulin stimulates glucose uptake in insulin sensitive tissues, mainly skeletal muscle, and it inhibits glucose production in the liver and promotes the storage of glycogen in liver and skeletal muscle. It promotes the delivery of non-esterified fatty acids (NEFA) to adipose tissue where they are stored as triglycerides and lipolysis in fat cells is inhibited. In general, overall protein synthesis is increased.

Recent research suggests that there is a high expression of the cytokine tumor necrosis factor-α (TNF-α) in the adipocytes of obese individuals, and that this TNF-α is a principal contributor to insulin resistance and its subsequent type 2 diabetes of obesity. TNF-α is an important regulator of the processes of apoptosis and thus modulates the volume of tumor, adipose and muscular tissues. It is produced not only by immunocompetent cells but also by adipocytes and muscle cells. This cytokine is activated in tumors and obesity, among other conditions. By acting on the phosphorylation of IRS-1 and phosphatidylinositol 3-kinase (PI-3), by modifying resistance through regulation of the synthesis of the insulin responsive glucose transporter GLUT4, and through interference with insulin signaling (perhaps via leptin), TNF-α promotes insulin resistance and anorexia.

Irrespective of the cause, insulin resistance is associated with widespread and adverse effects on health. This is true even when glucose tolerance is only mildly impaired but not yet in the overt diabetic range. Notable among the adverse effects is the predisposition to vascular disease affecting large blood vessels and an association with hypertension and dyslipidemia (elevated triglycerides and decreased HDL). In fact, this combination of 1) glucose intolerance, 2) insulin resistance, 3) hypertension and 4) dyslipidemia is common enough to have acquired the name Syndrome X, the insulin resistance syndrome or Reaven's syndrome. Clinically it defines hundreds of millions of people worldwide.

OBJECTIVES OF THE INVENTION

In view of the foregoing discussion, pyrone-indole derivatives would be of therapeutic use for a variety of maladies and conditions, particularly those associated with melatonin, 5-HT, insulin and GABAergic disregulation. The present invention addresses the need for more therapeutically advanced compounds than those aimed at modulating one of these classes alone. Such an agent acting as MT-1 and MT-2 or serotonin receptor agonists/antagonists with additional GABA receptor modulation properties can provide new drugs with, but not limited to, sedative efficacy with additional clinical benefits, such as sleep improvement with beneficial effects on daytime vigilance. Due to this unique mode of action, these agents will not display typical side effects related to benzodiazepines, such as tolerance and drug discontinuation symptoms.

In addition, the present invention addresses the need for new melatoninergic derivatives affecting insulin resistance and type II diabetes.

The entire contents of the above-cited patents, patent applications and literature articles are deemed to be incorporated herein by reference.

SUMMARY OF THE INVENTION

The invention relates to compounds having the formula (I):

wherein:

B represents:

—X—Y-Z- wherein

X represents —$(CH_2)_n$— (wherein n is 0-6) in which the alkyl moiety is linear or branched, Y represents oxygen, sulphur, >NH or is absent, Z represents >C=O, >O, >COO or is absent, wherein at least one of X, Y and Z must be present;

Ar represents an indole nucleus ring system:

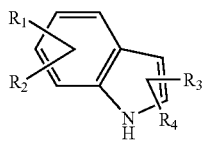

Ar' represents an alpha-, beta- or gamma-pyrone nucleus ring system:

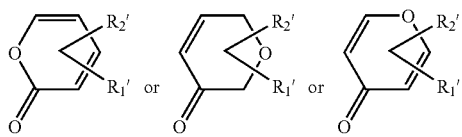

wherein each of $R_{1-4}$ substitutes the ring Ar at any available position (including the N-position) and each of $R_{1'-2'}$ substitutes the ring Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen and sulphur; a $C_{6-8}$ heteroaryl group containing 1-3 hetero atoms independently selected from nitrogen, oxygen or sulfur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen or sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{1-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the Ar ring not substituted by $R_1$ and $R_2$, including the N-position, and Ar' can be bonded to B at any carbon on the Ar' ring not substituted by $R_{1'}$ or $R_{2'}$;

or a pharmaceutically acceptable salt or stereoisomer thereof.

As used herein, "aryl" represents phenyl or naphthyl.

Without prejudice to the generality of the compounds of the present invention, a sub-group of presently preferred compounds is defined such that in formula (I), X is —$(CH_2)_2$—, Y is >NH or >0, Z is >C=O, Ar is an indole containing a bond, $R_3$, to X at position 3 of the indole ring, $R_1$ is methoxy on position 5 of the indole ring, each of $R_2$ and $R_4$ is hydrogen, and either (a) Ar' is a gamma-pyrone bonded to Z on position 2 of the pyrone ring, $R_{1'}$ is hydrogen or a hydroxy group at position 5 of the pyrone ring, and $R_{2'}$ is hydrogen or a carboxy group at position 6 of the gamma-pyrone ring, or (b) Ar' is an alpha-pyrone ring bonded to Z at position 5 of the pyrone ring, $R_{1'}$ and $R_{2'}$ are each hydrogen at positions 3, 4 or 6 of the pyrone ring; or a pharmaceutically acceptable salt or stereoisomer thereof.

The present invention also includes in its scope pharmaceutical compositions containing as an active substance a therapeutically effective amount of a compound of formula (I), or a pharmaceutically acceptable salt thereof as well as any stereoisomer, covered by formula (I), in association with one or more pharmaceutically acceptable diluents, preservatives, solubilizers, emulsifiers, adjuvants, excipients or carriers conventionally used in pharmaceutical and veterinary formulations. The present pharmaceutical formulation can be adopted for administration to humans and/or animals.

The compounds of formula (I) are useful for treating and/or preventing, and/or minimizing insulin resistance and diabetes type II, neuronal loss associated with stroke, ischemia, central nervous system (CNS) trauma, CNS disorders including neurodegenerative diseases (such as Alzheimer's disease, amyotrophic lateral sclerosis (ALS), Huntington's disease, Parkinson's disease and Down's syndrome); treating or preventing the adverse consequences of the overstimulation of the excitatory amino acids; treating or preventing psychiatric disorders, epilepsy and other convulsive disorders, anxiety, sleep disorders including insomnia, psychiatric diseases (e.g., depression, psychosis), chronic pain (analgesia), glaucoma, cytomegalovirus (CMV) retinitis and urinary incontinence, and inducing anesthesia, as well as enhancing cognition, and preventing and treating opiate tolerance and withdrawal symptoms.

By way of further elaboration or explanation of conditions which it is presently contemplated may be amenable to treatment by administration of the present compounds, such conditions include impotence; cardiovascular disorders (including hypertension); blood coagulation disorders; inflammatory disorders; neuropathy; chronobiological-based disorders (e.g., jet lag); circadian sleep disorders (such as delayed sleep syndrome, shift-work problems, and season-related disorders e.g. seasonal affective disorder (SAD)); endocrine indications (e.g., contraception and infertility, precocious puberty, premenstrual syndrome, hyperprolactinemia, and growth hormone deficiency); neoplastic diseases (including cancer and other proliferative diseases (benign and tumor prostate growth)); immune system disorders including AIDS; conditions associated with senescence; opthalmological diseases; cluster headache; migraine; skin-protection; diabetes stabilization and weight gain disorders (leptin, obesity); to provide skin protection and as an aid to animal breeding (e.g., regulation of fertility, puberty and pelage color).

DETAILED DESCRIPTION OF THE INVENTION

This invention relates to compounds having the formula (I):

wherein:

—B— represents:

X—Y-Z- wherein

X represents —$(CH_2)_n$— (wherein n is 0-6), in which the alkyl moiety is linear or branched, Y represents oxygen, sulphur, >NH or is absent;

Z represents >C=O, or >O, or >COO or is absent;

wherein at least one of X, Y and Z must be present;

ring system Ar represents an indole nucleus:

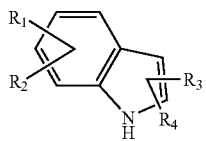

ring system Ar' represents an alpha-, beta- or gamma-pyrone nucleus:

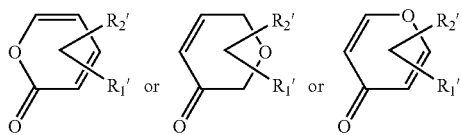

wherein each of the $R_{1-4}$ substitutes the ring systems Ar at any available position (including the N-position) and each of the $R_{1'-2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen and sulphur; a $C_{6-8}$ heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, arylalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing from 1-3 heteroatoms independently selected from nitrogen, oxygen and sulphur; a heteroaryl group containing from 1-3 hetero atoms independently selected from nitrogen, oxygen and sulphur; $C_{1-5}$ alkyl, $C_{2-5}$ alkenyl, $C_{2-5}$ alkynyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol; and either of $R_3$ or $R_4$ further can include or represent a bond to B;

wherein Ar can be bonded to B at any position on the Ar ring not substituted by $R_1$ and $R_2$ including the N-position, and Ar' can be bonded to B at any carbon on the Ar' ring not substituted by $R_{1'}$ or $R_{2'}$;

or a pharmaceutically acceptable salt or stereoisomer thereof.

As used herein, "aryl" represents phenyl or naphthyl.

Also as used herein, reference to "a" compound, salt or stereoisomer of formula (I) is intended to encompass "one or more" such compounds, salts or stereoisomers. Furthermore, reference to a "compound" of formula (I), as in the discussion below of pharmaceutical formulations, is also intended to include a salt or stereoisomer of the compound.

In a preferred embodiment, X is —$(CH_2)_n$—, wherein n is any of 0-6 and preferably any of 1-6, Y is >NH or >O and Z is >CO.

Without prejudice to the generality of the compounds of the present invention, in a preferred embodiment of the compounds defined by formula (I), X is —$(CH_2)_{2-}$, Y is >NH or >O, Z is >C=O, Ar is an indole containing a bond, $R_3$ to X at position 3 of the indole ring, $R_1$ is methoxy on position 5 of the indole ring, each of $R_2$ and $R_4$ is hydrogen, Ar' is a gamma-pyrone bonded to Z at position 2 of the pyrone ring, $R_{1'}$ is hydrogen or a hydroxy group at position 5 of the pyrone ring and $R_{2'}$ is hydrogen or a carboxy group at position 6 of the gamma pyrone ring; or a pharmaceutically acceptable salt or stereoisomer thereof. In a second preferred embodiment, Ar is as defined above and Ar' is an alpha-pyrone ring bonded to Z at position 5 of the alpha-pyrone ring and $R_{1'}$ and $R_{2'}$ are hydrogens; or a pharmaceutically acceptable salt or stereoisomer thereof.

The present invention also includes within its scope the preparation of compositions containing a compound of formula (1) wherein the compositions are useful as medicaments. The pharmaceutical compositions contain as an active substance a therapeutically effective amount of a compound of formula (I) or a pharmaceutically acceptable salt thereof as well as any stereoisomer covered by formula (I); in association with one or more pharmaceutically acceptable diluents, preservatives, solubilizers, emulsifiers, adjuvant, excipients and carriers conventionally used in pharmaceutical and veterinary formulations. The present pharmaceutical formulations can be adapted for administration to humans and/or animals.

A pharmaceutical formulation according to the invention preferably is characterized by at least one of the following features:

(i) it is adapted to be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration;

(ii) it is in unit dosage form, each unit dosage comprising an amount of at least one compound of formula (I) which is within the range of about 2.5 µg to 25 mg/kg body weight;

(iii) it is an extended release formulation, wherein at least one compound of formula (I) is released at a predetermined controlled rate.

The formulations further can be characterized in that they can be administered alone or in combination with or in conjunction with other compounds which are known in the art to be useful for the prevention and treatment of central nervous system (CNS) disorders and metabolic disorders, including, but not limited to, neurodegenerative diseases, sleep disorders, insulin resistance and diabetes type II.

Suitable pharmaceutically acceptable salts of the compounds of formula (I) of use in the present invention include salts which may, for example, be formed by mixing a solution of the compound with a solution of a pharmaceutically acceptable non-toxic acid, such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

The compounds of formula (I) can be administered to mammals to treat and/or prevent insulin resistance and diabetes type II; neuronal loss associated with stroke; ischemia; central nervous system (CNS) trauma; CNS disorders including neurodegenerative diseases (such as Alzheimer's disease, amyotrophic lateral sclerosis (ALS), Huntington's disease, Parkinson's disease and Down's syndrome); the adverse consequences of the overstimulation of the excitatory amino acids; psychiatric diseases; epilepsy and other convulsive disorders; anxiety; sleep disorders including insomnia; psychiatric diseases (e.g., depression, psychosis); chronic pain (analgesia); glaucoma; cytomegalovirus (CMV) retinitis; urinary incontinence; and opiate tolerance and withdrawal symptoms. The compounds also can be administered to induce anesthesia, as well as to enhance cognition.

In addition, the compounds of the invention can be administered to a mammal to treat and/or prevent impotence; cardiovascular disorders (including hypertension, blood coagulation disorders); inflammation disorders; neuropathy; chronobiological-based disorders (e.g., jet lag); circadian sleep disorders (such as delayed sleep syndrome, shift-work problems, and seasonal-related disorders (e.g. seasonal affective disorder (SAD)); endocrine indications (e.g., contraception, infertility, precocious puberty, premenstrual syndrome, hyperprolactinemia, and growth hormone deficiency); neoplastic diseases (including cancer and other proliferative diseases (benign and tumor prostate growth)); immune system disorders including AIDS; conditions associated with senescence; opthalmological diseases; cluster headache; migraine; weight gain disorders (leptin, obesity); to provide skin protection and as an aid to animal breeding, e.g., regulation of fertility, puberty and pelage color.

As used herein "to treat" means to alleviate or cure a disease, disorder or condition or to ease at least one symptom of the disease, disorder or condition.

In preferred embodiments, the disease or disorder is one suffered by humans and the compounds of the invention are administered to humans.

The compounds of the invention can be administered alone or in combination with other agents known to be beneficial in treating the disease, disorder or condition to be treated. As used herein, "in combination" means that the compound of formula (I) and the other agent can be co-administered, either in concomitant therapy or in a fixed physical combination, or they may be administered at separate times but so as to complement one another.

In a preferred embodiment, compounds of formula (I) can be administered to alter circadian rhythms or to improve sleep quality, or to treat or prevent sleep disorders or sleep disturbances in a mammal, especially a human. In addition, the compounds of formula (I) can be administered to increase sleep efficiency and to augment sleep maintenance. Sleep disorders and sleep disturbances which can be treated or prevented through the administration of compounds of formula (I) include sleep problems associated with insomnia, hypersomnia, sleep apnea, narcolepsy, nocturnal myoclonus, REM sleep interruptions, jet-lag, shift workers' sleep disturbances, dysomnias, night terror, insomnias associated with depression or with emotional mood disorders and sleep walking and enuresis, as well as sleep disorders which accompany aging, conditions associated with circadian rhythmicity, mental and physical disorders associated with travel across time zones and with rotating shift-work schedules or syndromes such a fibromyalgia which are manifested by non-restorative sleep and muscle pain or sleep apnea which is associated with respiratory disturbances during sleep.

In the treatment or prevention of the foregoing conditions, broadly defined as circadian rhythm disorders or sleep disorders, the compound of formula (I) can be administered alone or in combination with other compounds known in the art to be useful for enhancing sleep quality and preventing and treating sleep disorders and sleep disturbances, including e.g., sedatives, hypnotics, anxiolytics, antipsychotics, antianxiety agents, minor tranquilizers, melatonin agonists and antagonists, melatonin, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, eszopiclone, ethchlorvynol, etomidate, fenobam, flunitrazepam, flurazepam, fluvoxamine, fluoxetine, fosazepam, gaboxadol, glutethimide, halazepam, hydroxyzine, imipramine, indiplon, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, zopiclone and salts thereof, and combinations thereof, and the like.

Combinations of one or more of these known therapeutic agents with a compound of formula (I) will provide additional, complementary, and often synergistic effects to enhance the desirable properties of the known therapeutic agent.

The compound of formula (I), alone or in combination with one of the aforementioned known therapeutic agents further can be administered in combination with physical treatment methods, such as light therapy (such as described in U.S. Pat. Nos. 5,447,527 and 5,562,719, both of which are incorporated herein by reference).

In another embodiment, compounds of formula (I) can be administered in combination with an antidiabetic agent, such as insulin, sulfonylureas, biguanides (such as metformin), alpha-glucosidase inhibitors (such as acarbose), peroxisome proliferator-activated receptor gamma (PPARgamma) agonists such as thiazolidinediones, including pioglitazone and rosiglitazone, cholesterol lowering agents such as HMG-CoA reductase inhibitors (lovastatin, simvastatin, pravastatin, fluvastatin, atorvastatin, rivastatin, itavastatin, and other statins), sequestrants (cholestyramine, colestipol and dialkylaminoalkyl derivatives of a cross-linked dextran); nicotinyl alcohol, nicotinic acid or a salt thereof, PPARalpha agonists (gemfibrozil, clofibrate, fenofibrate and bezafibrate), probucol, PPARalpha/gamma agonists, such as KRP-297, antiobesity agents, such as fenfluramine, dexfenfluramine, phentiramine, subitramine, orlistat, neuropeptide Y5 inhibitors, beta adrenergic receptor agonists, dipeptidyl peptidase-4 inhibitors, and PTP-1B inhibitors.

When a compound of formula (I) is administered in combination with another therapeutic agent, such as an anti-diabetic agent or an agent for treating a sleep disorder or circadian rhythm disorder, the compound of formula (I) and the known therapeutic agent can be administered independently in a daily dosage which ranges from one one-hundredth to one times the dosage levels which are effective when the compounds are administered alone.

Compounds of formula (I) can be formulated into pharmaceutical composition suitable for oral, parenteral (e.g., intramuscular, intraperitoneal, intravenous or subcutaneous injection, or implant) nasal, vaginal, rectal, sublingual or topical routes of administration. The compositions can comprise one or more pharmaceutically acceptable diluents, preservatives, solubilizers, emulsifiers, adjuvants, excipients and/or carriers.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. In the case of capsules, tablets and pills, the dosage forms may also comprise buffering agents. When the dosage unit form is a capsule, it may contain, in addition to materials of the above type, a liquid carrier such as a fatty oil. Various other materials can be present as coatings or to otherwise modify the physical form of the dosage unit. Tablets and pills can additionally be prepared with enteric coatings and tablets may be coated with shellac, sugar or both.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring, and perfuming agents. A syrup or elixir may contain the active compound, sucrose as a sweetening agent, methyl and propyl parabens as preservatives, a dye and a flavoring such as cherry or orange flavor.

Preparations according to this invention for parenteral administration include sterile aqueous or non-aqueous solutions, suspensions, or emulsions. Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like may be incorporated as required. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions that can be dissolved in sterile water, or some other sterile injectable medium immediately before use.

Compositions for rectal or vaginal administration are preferably suppositories that may contain, in addition to the active substance, excipients such as cocoa butter or a suppository wax. Compositions for nasal or sublingual administration are also prepared with standard excipients well known in the art.

The dosage of active agent in compositions of this invention can vary, provided that a therapeutic amount is administered. Desirably the active agent is administered to a patient (human or animal) in need of such treatment in dosages that will provide optimal pharmaceutical efficacy. The selected dosage depends upon the nature and severity of the disease or disorder to be treated, desired therapeutic effect, the route of administration, and the duration of treatment. Dosage amount also can vary depending on the weight of the patient, and other factors. For example, the effect of a compound of formula (I) that induces a phase shift in a central circadian pacemaker may be dependent on both the ambient and circadian time of administration. The same compound may induce a phase advance, a phase delay or have a minor effect on a particular circadian rhythm depending on the circadian time of administration. The dose will vary from patient to patient depending on the nature and severity of the disease, the patient's weight, special diets then being followed by the patient, concurrent medication, the bioavailability of the compound upon administration and other factors which those skilled in the art will recognize.

In the treatment of a condition in accordance with the present invention, an appropriate daily dosage level will generally be about 2.5 µg to 25 mg per kg patient body weight. The daily dosage amount can be administered in single or multiple doses per day. Preferably, the dosage level will be about 2.5 µg to about 20 mg/kg patient body weight; more preferably about 2.5 μg to about 10 mg/kg patient body weight. For example, for achieving a circadian rhythm phase-shifting effect, resetting the internal circadian clock, shortening the time of reintrainment of circadian rhythms, alleviating a circadian rhythm disorder or enhancing the quality of sleep, a suitable dosage level is about 2.5 μg to 25 mg/kg patient body weight, preferably about 2.5 μg to 20 mg/kg patient body weight, and especially about 2.5 μg to 10 mg/kg patient body weight. In larger mammals, for example humans, a typical indicated daily dose for oral administration is about 0.2 to about 1000 mg. Preferably the daily oral dosage is within the range of about 0.5 to about 50 mg. and more preferably within the range of about 2.5 to about 20 mg. When using an injectable or topical formulation, a preferred dosage level is about 2.5 μg to 5 mg/kg patient body weight, and especially about 2.5 μg to 1 mg/kg patient body weight. In larger mammals, for example humans, a typical indicated dose is about 100 μg to 100 mg i.v. A compound can be administered in a regimen of once to several times per day, for example 1 to 4 times per day, preferably once or twice per day.

Formulations of this invention can be in the form of immediate release, or, where appropriate, such as solid formulations for oral administration, can be in extended release forms. Extended release formulations include delayed-, sustained-, pulsed- or controlled-release formulations. Suitable extended release formulations useful for purposes of the present invention include the types of formulations described in U.S. Pat. Nos. 6,106,864; 7,053,122; and 7,118,762, incorporated herein by reference. Details of other types of suitable release technologies, such as high energy dispersions and osmotic and coated particles can be found, for example, in Verma, R. and S. Garg, *Pharmaceutical Technology On-Line*, 25(2), 1-14 (2001), also incorporated herein by reference.

The period of time in which an extended release formulation releases the compound varies based upon the indication and the target therapeutic levels. For insomnia, for example, it is desirable to limit the pharmacological effects of the compound administered to night-time, e.g. about 8 hours. For anti-diabetes treatment, it is desirable for the compound to have effect continuously, e.g., 12 hour effectiveness with administration of the formulation twice a day, morning and evening.

The invention will be illustrated by the following Examples. The following examples are understood to be illustrative only and are not intended to limit the scope of the present invention in any way.

EXAMPLE 1

N-[2-(5-methoxy-indol-3-yl)-ethyl]-commenamide

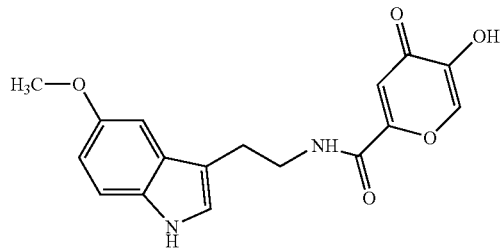

Reaction Scheme for the synthesis of the synthesis of N-[2-(5-methoxy-indole-3-yl)-ethyl]-commenamide

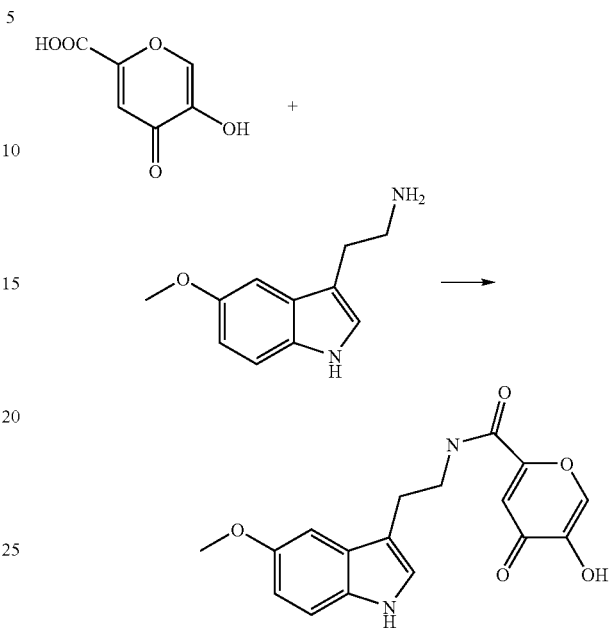

General procedure of the synthesis of N-[2-(5-methoxy-indole-3-yl)-ethyl]-commenamide Under an argon atmosphere, a 100 ml three-necked flask round-bottom flask was charged with comenic acid (560 mg, 1 equiv.) and 5-methoxytryptamine (750 mg, 1.1 equiv.), dissolved in DMF (20 ml), and brought to 0° C. by means of an ice-bath. HOBt (1-hydroxybenxotriazole monohydrate, 535 mg, 1.1 equiv.), EDC (1-(3-dimethylaminopropyl)-3-ethylcarbodiimide hydrochloride, 760 mg, 1.1 equiv.) and triethylamine (1.25 ml, 2.5 equiv.) were then added with magnetic stirring. The mixture was stirred for an additional 15 minutes at 0° C. and subsequently allowed to react for 48 h at room temperature. Water (25 ml) was then added and the mixture was extracted thoroughly with dichloromethane (6×30 ml). The combined organic phases were dried over $Na_2SO_4$ and the solvent was removed by rotary evaporation. The crude component was chromatographed over a silica gel column by eluting with dichloromethane/methanol 95/5. The product was recovered as a thick oil, which was stripped three times with diethyl ether to furnish a brown solid (180 mg, yield, 15%).

Experimental data for N-[2-(5-methoxy-indol-3-yl)-ethyl]-commenamide

MS (ESI POS): 329 (M+H), 351 (M+Na), 392 (M+Na+$CH_3CN$)

HPLC assay: 97%

$^1$H NMR ($CDCl_3$ 400 MHz) δ 3.06 (t, j=6.7 Hz, 2H, $CH_2CH_2NH$), 3.76-3.79 (m, 2H, $CH_2$, $CH_2NH$), 3.84 (s, 3H $OCH_3$), 6.32 (br s, 1H, OH), 6.76 (br s, 1H, $CH_2CH_2NH$), 6.9 (dd, $J_1$=2.3 Hz, $J_2$=8.8 Hz, 1H aromatic H), 7.04 (d, J=2.3 Hz, 1H, aromatic H), 7.06 (d, J=2.3 Hz, 1H, aromatic H), 7.27 (s, 1H, CH), 7.29 (d, J=8.8 Hz, 1H, aromatic H), 7.73 (s, 1H, CH), 7.96 (br s, 1H, NH).

EXAMPLE 2

O-[2-(5-methoxy-indole-3-yl)-ethyl]-comenic ester

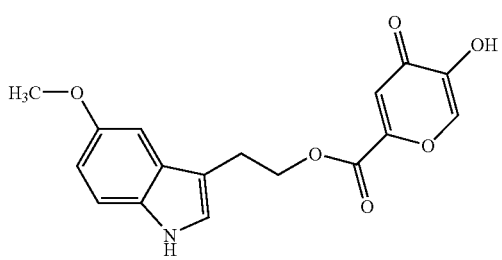

Reaction Scheme for the synthesis of
O-[2-(5-methoxy-indol-3-yl)-ethyl]-comenic ester

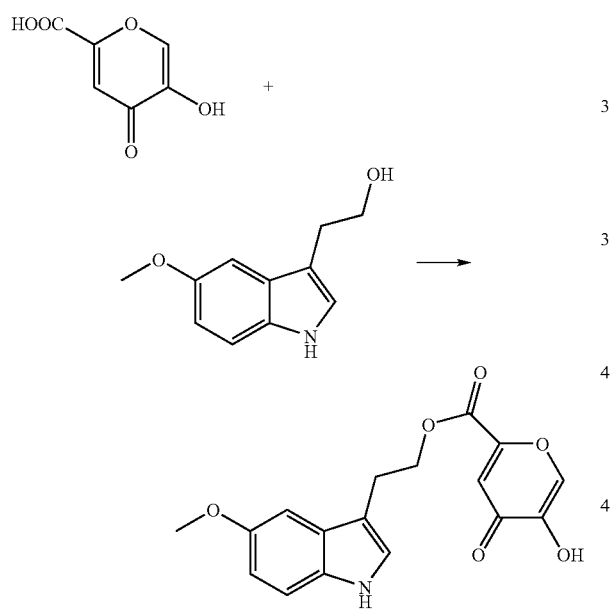

Under an argon atmosphere, a 100 ml three-necked round-bottom flask was charged with comenic acid (300 mg, 1 equiv.) and 5-methoxytryptophol (365 mg, 1 equiv.) dissolved in CH$_2$Cl$_2$/DMF (10/5 ml, respectively). DDC (dicyclohexylcarbodiimide, 435 mg. 1.1 equiv.) and DMAP (4-dimethylaminopyridine, 45 mg, 0.2 equiv.) were then added with magnetic stirring. After the mixture was stirred for 16 hours at room temperature, the white precipitate that formed was discarded by filtration through a Buchner funnel. From the clear filtrate, the solvent was removed by rotary evaporation. The crude was then chromatographed over a silica gel column by eluting with 250 ml of CH$_2$Cl$_2$ followed by dichloromethane/methanol 97/3. Fractions containing the product were combined and concentrated and the resulting solid was recrystallized from cyclohexane/ethyl acetate. The pure O-[2-(5-methoxy-indol-3-yl)-ethyl]-comenic ester was obtained as a light yellow solid (250 mg, yield 40%).

Experimental data for
O-[2-(5-methoxy-indol-3-yl)-ethyl]-comenic ester

MS (ESI POS): 330 (M+H), 352 (M+Na), 393 (M+Na+CH$_3$CN)

HPLC assay: 97%

$^1$H NMR (CDCl$_3$ 400 MHz) δ 3.18-3.22 (m, 2H, CH$_2$CH$_2$O), 3.87 (s, 3H, OCH$_3$), 4.60-4.64 (m, 2H, CH$_2$CH$_2$O), 6.40 (br s, 1H, OH), 6.88 (dd, J$_1$=2.2 Hz, J$_2$=8.8 Hz, 1H, aromatic H), 7.06-7.08 (m, 2H, aromatic H+CH), 7.22 (s, 1H, aromatic H), 7.25-7.28 (m, 1H, aromatic H), 7.96-8.0 (s+br s, 2H, NH+CH).

EXAMPLE 3

N-[2-5-methoxy-indol-3-yl)-ethyl]-chelidonamide

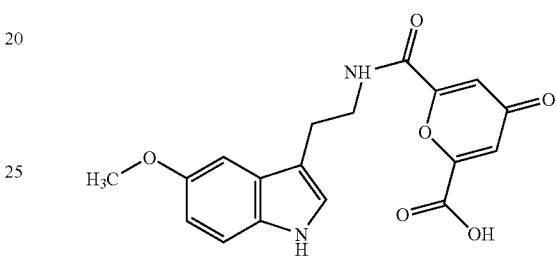

Reaction Scheme for the synthesis of N-[2-(5-methoxy-indole-3-yl)-3-ethyl]-chelidonamide

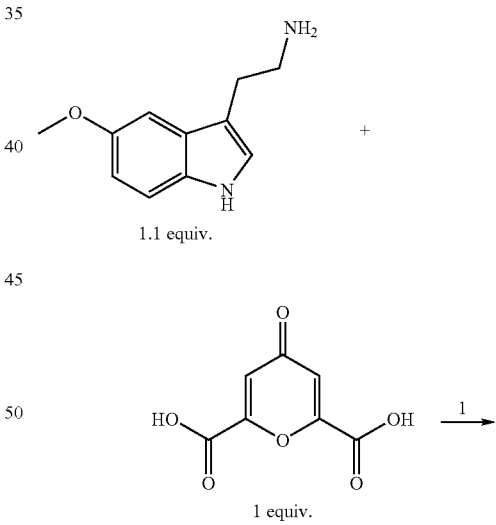

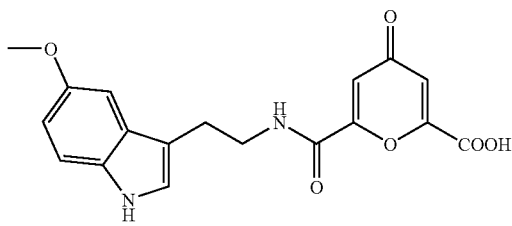

Yield 11%
i) DMF, HOBt 1.1 equiv., EDC 1.1 equiv., NEt$_3$ 2.5 equiv., r.t., 24 h.

General Procedure for the synthesis of N-[2-(5-methoxy-indol-3-yl)-ethyl]-chelidonamide In a 100 ml four-necked round-bottom flask kept under an argon atmosphere 5-methoxytryptamine (350 mg, 1.1 equiv.) was dissolved in 10 ml of DMF. Under magnetic stirring chelidonic acid (310 mg, 1.1 equiv) was added. The resulting solution was brought to 0° C. by means of an ice-bath and HOBt (1-hydroxybenxotriazole monohydrate, 250 mg, 1.1 equiv.), EDC (1-(3-dimethylaminopropyl)-3-ethylcarbodiimide hydrochloride, 350 mg, 1.1 equiv.) and triethylamine (0.6 ml, 2.5 equiv.) were then added under magnetic stirring. The mixture remained stirring for an additional 15 minutes at 0° C. and was subsequently allowed to react for 48 h at room temperature. The reaction course was followed by HPLC-MS. Precipitated materials were removed by filtration. Water (100 ml) was added to the filtrate and the mixture was extracted with dichloromethane (3×50 ml). The combined organic phases were dried over $Na_2SO_4$ and the solvent was removed by rotary evaporation. The crude was then chromatographed over a silica gel column by initial elution with dichloromethane/ethanol 8/2. After elution of a side product, the polarity of the eluant was increased (dichloromethane/ethanol 1/1) and the product was recovered as a pale yellow solid (70 mg, yield 11%).

Experimental data for N-[2-(5-methoxy-indol-3-yl)-ethyl]-chelidonamide

MS (ESI POS): 357 (M+H), 374 (M+Na), 398 (M+H+$CH_3CN$)

HPLC assay: 97%

$^1$H NMR (DMSO-$d_6$ 400 MHz) δ 2.91 (t, J=7.5 Hz, 2H, $CH_2CH_2NH$), 3.50-3.55 (m, 2H, $CH_2CH_2NH$), 3.76 (s, 3H, $OCH_3$), 6.64-6.71 (m, 3H), 7.07 (d, J=2.6 Hz, 1H), 7.13 (d, J=2.1 Hz, 1H), 7.20 (d, J=8.8 Hz, 1H), 8.29 (s, 1H, NH), 8.92 (br t, J=5.8 Hz, 1H, $CH_2CH_2NH$), 10.62 (br s, 1H, COOH).

EXAMPLE 4

N-[2-(5-methoxy-indol-3-yl)-ethyl]-coumalylamide

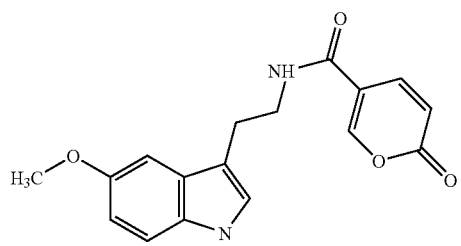

General procedure for the synthesis of N-[2-(5-methoxy-indol-3-yl)-ethyl]-coumalylamide

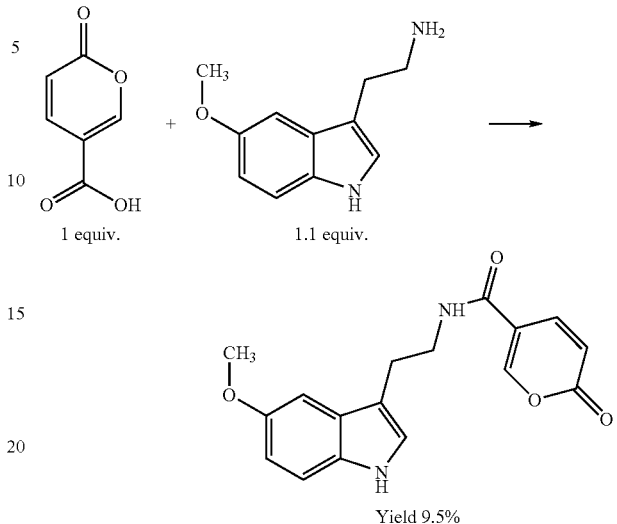

Yield 9.5%

Under an argon atmosphere, a 100 ml three-necked round-bottom flask was charged with coumalic acid (600 mg, 1 equiv.) and 5-methoxytryptamine (900 mg. 1.1 equiv.), dissolved in DMF (25 ml), and brought to 0° C. by means of an ice-bath. HOBt (1-hydroxybenxotriazole monohydrate, 640 mg, 1.1 equiv.), EDC (1-(3-dimethylaminopropyl)-3-ethyl-carbodiimide hydrochloride, 900 mg, 1.1 equiv.) and triethylamine (1.5 ml, 2.5 equiv.) were then added under magnetic stirring. The mixture was stirred for an additional 15 minutes at 0° C. and subsequently allowed to react for 48 h at room temperature. The reaction course was followed by HPLC-MS. Water (40 ml) was then added and the mixture was extracted thoroughly with dichloromethane (6×30 ml). The combined organic phases were dried over $NA_2SO_4$ and the solvent was removed by rotary evaporation. The crude was then chromatographed over a silica gel column by eluting with dichloromethane/methanol 95/5 and the product was recovered (130 mg, 9.5% yield).

Experimental data for N-[2-(5-methoxy-indol-3-yl)-ethyl]-coumalylamide

MS (ESI POS): 313 (M+H), 335 (M+Na), 376 (M+Na+$CH_3CN$)

HPLC assay: 95%

$^1$H NMR ($CDCl_3$, 400 MHz) δ 3.09 (t, J=6.1 Hz, 2H, $CH_2CH_7NH$), 3.70-3.74 (m, 2H, $CH_2CH_2NH$), 3.87 (s, 3H, $OCH_3$), 5.58 (d, J=8.8 Hz, 1H, CH), 6.88-7.04 (m, 5H, 4 aromatic H+1 CH), 7.29 (d, J=8.8 Hz, 1H, CH), 8.03 (br s, 1H, NH), 9.65 (br s, 1H, $CH_2CH_2NH$).

EXAMPLE 5

N-[2-(2-bromo-5-methoxy-indol-3-yl)-ethyl]-coumalylamide

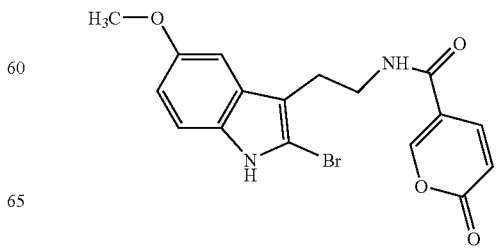

Reaction Scheme for the synthesis of
N-[2-(5-methoxy-indol-3-yl)-ethyl]-coumalylamide

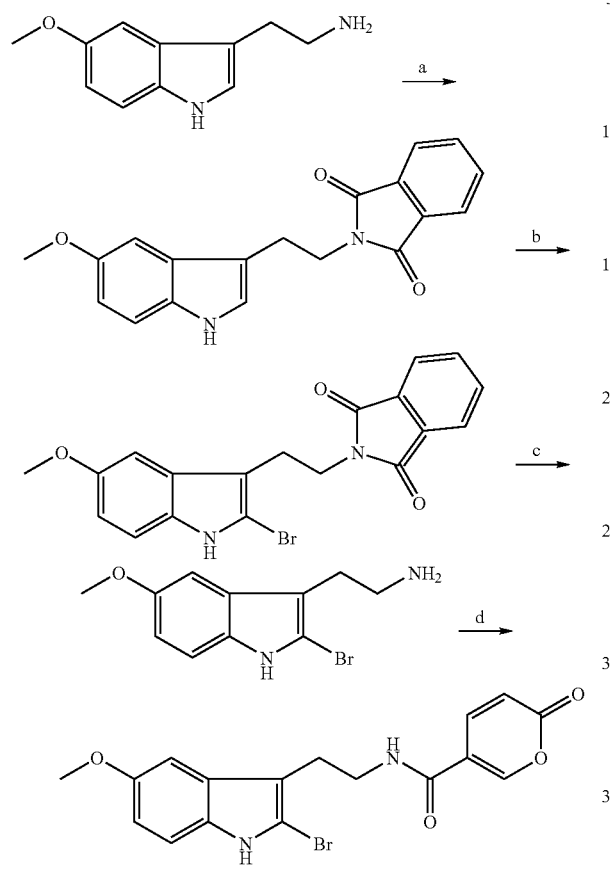

a) phthalic anhydride, TEA, toluene, reflux, overnight
b) pyridinium tribromide, THF/chloroform, -10° C., 30 min
c) methylamine, EtOH, rt, 3 hr
d) coumalic acid, NMM, TBTU, DMF, rt, 5 hr a. 5-methoxytryptamine and phthalic anhydride were refluxed in toluene for 16 hours. Concentration of the reaction under reduced pressure gave the crude product that was used in the next step without further purification.

b. Crude phthaloyltryptamine was dissolved in THF:CHCl$_3$ (1:1) and the resulting solution was cooled to –10° C. and then treated with pyridinium bromide perbromide. The reaction was checked by TLC and was allowed to warm to room temperature; CH$_2$Cl$_2$ was added. The solution was washed with saturated aqueous Na$_2$S$_2$O$_3$ and the aqueous layers were extracted with CH$_2$Cl$_2$. The combined organic layers were dried (MgSO$_4$), filtered, concentrated under reduced pressure, and the crude product was used in the next step without further purification.

c. The phthalimido group was removed by treatment of aqueous methylamine in ethanol at room temperature.

d. N-methylmorpholine was added to a solution of coumalic acid in dimethylformamide followed by 2-(1H-benzotriazol-1-yl)-1,1,3,3-tetramethyluronium tetrafluoroborate (TBTU) under an atmosphere of nitrogen. After the reaction mixture stirred for 20 min at room temperature, 5-methoxytryptamine was added slowly and the mixture was stirred for 5 hr. DMF from the reaction mixture was removed under high vacuum. The solid product was dissolved in CH$_2$Cl$_2$ and the resulting organic fraction was washed with 0.2N HCl, 0.2N NaHCO$_3$ and water and then dried (MgSO$_4$), filtered and concentrated under reduced pressure. The resulting product was purified with column chromatography.

Experimental data for N-[2-(2-bromo-5-methoxy-indol-3-yl)-ethyl]-coumalylamide $^1$H NMR (CDCl$_3$, 300 MHz) δ 10.00 (s, 1H, NH), 8.00 (s, 1H, Aromatic COOCH), 7.06 (t, 1H, J=9 Hz, CONH), 6.78-6.67 (m, 4H, Aromatic H), 5.41 (d, 1H, J=9.6 Hz, Aromatic COCH), 3.67 (s, 3H, OCH$_3$), 3.52 (q, 2H, J=6.24 Hz), 2.87 (t, 2H, J=6.3 Hz)

EXAMPLE 6

N-[2-(5-methoxy-indol-3-yl)-ethyl]-comanilamide

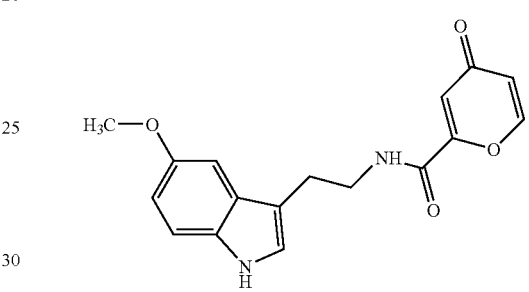

Reaction Scheme for the synthesis of
N-[2-(5-methoxy-indol-3-yl)-ethyl]-comanilamide

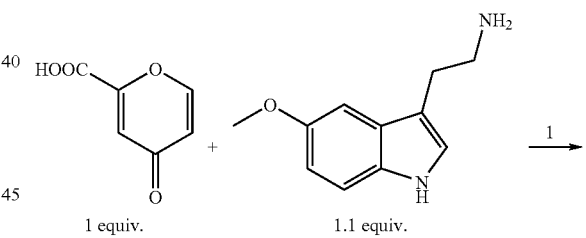

1 equiv.     1.1 equiv.

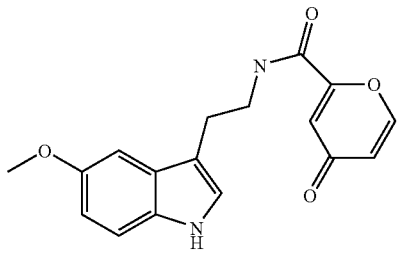

Yield 21%
i) DMF, HOBt 1.1 equiv., EDC 1.1 equiv., NEt$_3$ 2.5 equiv., r.t., 6 h.

General procedure for the synthesis of
N-[2-(5-methoxy-indol-3-yl)-ethyl]-comanilamide Under an argon atmosphere, a 100 ml three-necked flask round-bottom flask was charged with comanic acid (500 mg, 1 equiv.) and 5-methoxytryptamine (760 mg, 1.1 equiv.), dissolved in DMF (25 ml), and brought to 0° C. by means of an ice-bath. HOBt (1-hydroxybenxotriazole monohydrate, 530 mg, 1.1 equiv.), EDC (1-(3-dimethylaminopropyl)-3-ethylcarbodiimide hydrochloride, 750 mg, 1.1 equiv.) and triethylamine (1.25 ml, 2.5 equiv.) were then added under magnetic stirring. The mixture was stirred for an additional 15 minutes at 0° C. and subsequently allowed to react for 6 h at room temperature. The reaction course was followed by HPLC-MS. Water (50 ml) was then added and the mixture was extracted with dichloromethane (3×50 ml). The combined organic phases were dried over $Na_2SO_4$ and the solvent was removed by rotary evaporation. The crude was then chromatographed over a silica gel column by eluting with dichloromethane/methanol 95/5. The product was recovered as a bright yellow solid (235 mg, yield 21%).

Experimental data for
N-[2-(5-methoxy-indol-3-yl)-ethyl]-comanilamide

MS (ESI POS): 313 (M+H), 330 (M+$H_2O$), 335 (M+Na), 376 (M+Na+$CH_3CN$)

HPLC assay: 98%

$^1$H NMR (DMSO-$d_6$, 400 MHz) δ 2.88-2.92 (m, 2H, $CH_2CH_2NH$), 3.48-3.53 (m, 2H, $CH_2CH_2NH$), 3.75 (s, 3H, $OCH_3$), 6.42 (dd, $J_1$=2.3 Hz, $J_2$=5.9 Hz, 1H, CH=CH), 6.71 (dd, $J_1$=2.1 Hz, $J_2$=8.8 Hz, 1H, aromatic H), 6.78 (d, J=2.3 Hz, 1H, aromatic H), 7.04 (d, J=2.3 Hz, 1H, CH), 7.13 (d, J=2.1 Hz, 1H, aromatic H), 7.22 (d, J=8.8 Hz, 1H, aromatic H), 8.21 (d, J=5.9 Hz, 1H, CH=CH—CO), 9.04 (br t, J=5.8 Hz, 1H, $CH_2CH_2NH$), 10.65 (br s, 1H, NH).

EXAMPLE 7

N-[2-(5-methoxy-indol-3-yl)-ethyl]-2-methoxy-commenamide

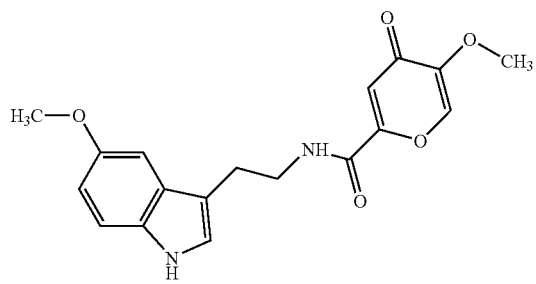

Reaction Scheme for the synthesis of N-[2-(5-methoxy-indol-3-yl)-ethyl]-2-methoxycommenamide

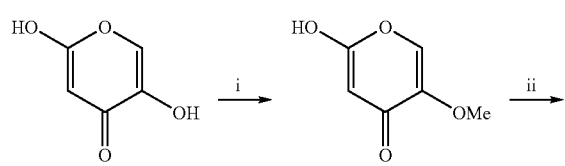

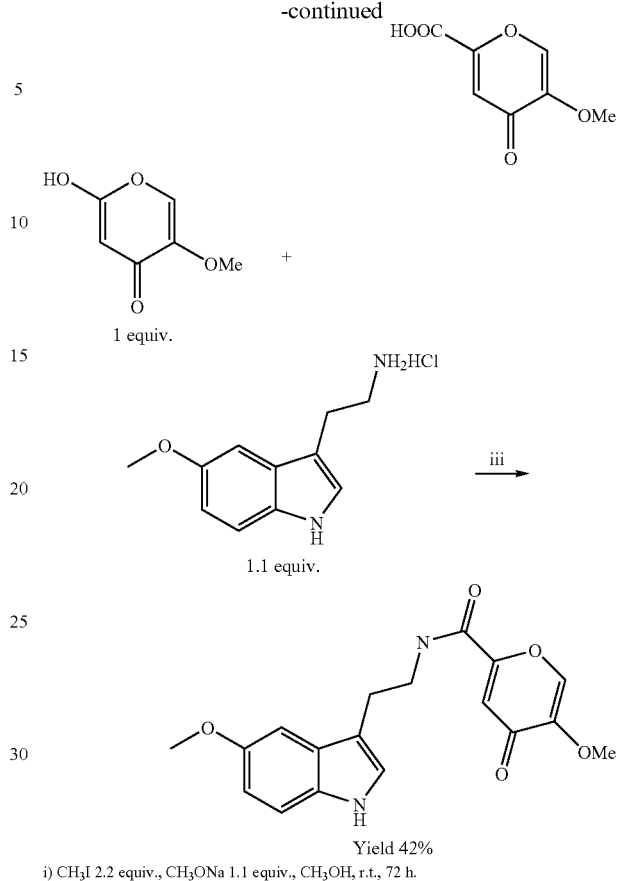

Yield 42% i) $CH_3I$ 2.2 equiv., $CH_3ONa$ 1.1 equiv., $CH_3OH$, r.t., 72 h.
ii) $MnO_2$ 16 equiv., $CH_3OH$, reflux, 1.5 h; $Ag_2O$ 1 equiv., $H_2O$, NaOH 1 N, r.t., 1 h.
iii) HOBt 1.1 equiv., EDC 1.1 equiv., $NEt_3$ .5 equiv., r.t., 16 h.

General procedure for the synthesis of N-[2-(5-methoxy-indol-3-yl)-ethyl]-2-methoxycommenamide i. In a 250 ml four-necked round-bottom flask kept under an argon atmosphere, 3.2 g of kojic acid (1 equiv.) were dissolved in 80 ml of methanol. Sodium methoxide in methanolic solution (4.6 ml, 1.1 equiv.; Fluka, 5.4 M) was then added under magnetic stirring in one portion. After 15 minutes, a solution of 2.95 ml (1.1 equiv.) of methyl iodide in 10 ml of $CH_3OH$ was added dropwise thereto and the resulting solution was allowed to react at room temperature. The reaction course was followed by TLC (dichloromethane/methanol 9/1 as the eluent). After 7 hours the conversion was approximately 50%, therefore another 1.1 equivalent of $CH_3I$ (2.95 ml in 10 ml of $CH_3OH$) was added. The reaction mixture was then reacted under stirring at room temperature for an additional 65 hours after which water (400 ml) was added. The solution was concentrated to a residual volume of ca. 25-30 ml and left at 4° C. for 14 h. The resulting precipitate was collected by filtration, washed with diethyl ether and dried under vacuum at 50° C. 2-Hydroxymethyl-5-methoxy-4-pyranone was recovered as a yellow crystalline solid (2.2 g, yield 63%).

ii. In a 250 ml round-bottom flask, 2-hydroxymethyl-5-methoxy-4-pyranone (2.2 g, 1 equiv.) was dissolved in 85 ml of methanol and 19.6 g of active manganese dioxide were added (16 equiv.). The reaction mixture was heated under reflux for 1.5 h, then cooled to room temperature. The insoluble part was filtered out and the remaining filtrate solution was concentrated to ca. a third of the initial volume. To this, 30 ml of water, 10 ml of NaOH 1 N and 3.3 g of silver oxide (1 equiv.) were added. The resulting mixture was reacted for 1 h at room temperature and was then filtered over a celite pad to eliminate salts. The filtrate was concentrated under reduced pressure to remove methanol therefrom and then washed with dichloromethane. Subsequently HCl 2 N (12 ml) was added to the water-soluble phase to form a precipitate which was collected by filtration, washed with diethyl ether and dried under vacuum at 50° C. 5-Methoxy-4-oxo-4H-pyran-2-carboxylic acid was obtained as a white solid (1.2 g, 50% yield).

ii. Under an argon atmosphere, a 100 ml three-necked round-bottom flask was charged with 5-methoxy-4-oxo-4H-pyran-2-carboxylic acid (340 mg, 1 equiv.) and 5-methoxytryptamine hydrochloride (500 mg, 1.1 equiv.), dissolved in DMF (15 ml), and brought to 0° C. by means of an ice-bath. HOBt (1-hydroxybenxotriazole monohydrate, 300 mg, 1.1 equiv.), EDC (1-(3-dimethylaminopropyl)-3-ethylcarbodiimide hydrochloride, 425 mg, 1.1 equiv.) and triethylamine (0.98 ml, 3.5 equiv.) were then added under magnetic stirring. The mixture was stirred for an additional 15 minutes at 0° C. and subsequently allowed to react for 16 h at room temperature. The reaction course was followed by HPLC-MS. Water (25 ml) was then added and the mixture was extracted with dichloromethane (2×30 ml). After a while a suspension appeared in the combined organic phases. The so-formed solid was then collected by filtration, washed with dichloromethane and dried at 50° C. The product was recovered as a white solid (210 mg). From the filtrate, the solvent was removed by rotary evaporation. The obtained solid residue was triturated with dichloromethane/petroleum ether and allowed to stand at room temperature for 24 h. The mixture was then filtered to furnish additional N-[2-(5-methoxy-indol-3-yl)-ethyl]-2-methoxy-commenamide (70 mg, 42% yield).

Experimental data for N-[2-(5-methoxy-indol-3-yl)-ethyl]-2-methoxy-commenamide

MS (ESI POS): 343 (M+H), 365 (M+Na), 406 (M+Na+CH$_3$CN)

HPLC assay: 98%

$^1$H NMR (DMSO-d$_6$, 400 MHz) δ 2.87-2.91 (m, 2H, CH$_2$CH$_2$NH), 3.47-3.52 (m, 2H, CH$_2$CH$_2$NH), 3.70 (s, 3H, OCH$_3$), 3.74 (s, 3H, OCH$_3$), 6.70 (dd, J$_1$=2.2 Hz, J$_2$=8.8 Hz, 1H, aromatic H), 6.83 (s, 1H, CH), 7.03 (d, J=2.8 Hz, 1H, aromatic H), 7.12 (d, J=2.2 Hz, 1H, aromatic H), 7.21 (d, J=8.8 Hz, 1H, aromatic H), 8.12 (s, 1H, CH), 9.02 (br t, J=5.7 Hz, 1H, CH$_7$CH2NH), 10.64 (br s, 1H, NH).

EXAMPLE 8

N-[2-(5-methoxy-indol-3-yl)-ethyl]-2-Pyrone-6-carboxamide

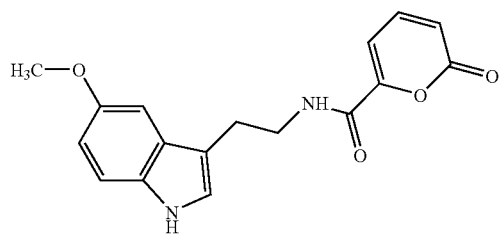

Reaction Scheme for the synthesis of N-[2-(5-methoxy-indol-3-yl)-ethyl-2-Pyrone-6-carboxamide

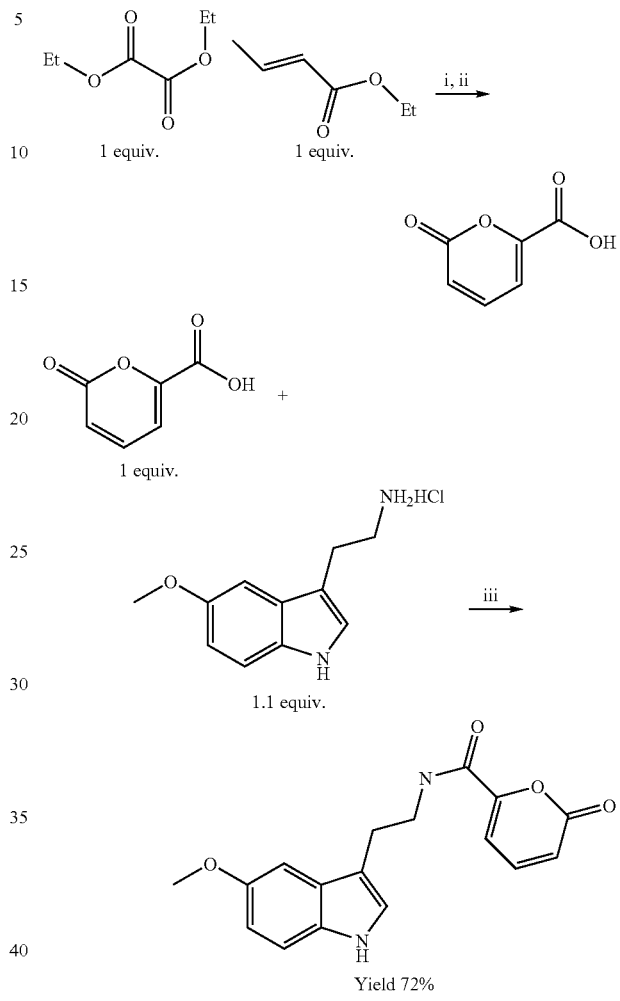

Yield 72%
i) KOEt 0.998 equiv., toluene, r.t., 18 h; H$_2$O/HCl 37%, r.t., 30 min.
ii) HCl 37%, 100° C., 6 h.
iii) DME, HOBt 1.1 equiv., EDC 1.1 equiv., Py 2.2 equiv., NEt$_3$ 1.4 equiv., r.t., 3

General procedure for the synthesis of N-[2-(5-methoxy-indol-3-yl)-ethyl]-2-Pyrone-6-carboxamide Step 1 & 2—In a 100 ml four-necked round-bottom flask kept under an argon atmosphere, 5.0 g of diethyl oxalate (1 equiv.) were dissolved in 35 ml of dry toluene. Potassium ethoxide (2.9 g, 0.998 equiv.) was then added under magnetic stirring in small portions. The internal temperature reached 40° C. and the initial suspension slowly turned into an orange solution. After 2 hours, the solution was brought to 0° C. by means of an ice-bath and ethyl crotonate (4.3 ml, 1 equiv.) was added dropwise over a period of 10 minutes. After 15 minutes from the end of the addition, the formation of a yellow precipitate of the potassium salt of 2,4-hexadiene-5-hydroxy-1,6-dioate was observed. The suspension was allowed to react at room temperature overnight. Subsequently the reaction mixture was filtered and the obtained yellow precipitate was washed with cyclohexane and diethyl ether and dried under vacuum at 50° C. to yield 4.9 g of a yellow solid. The latter was then dissolved in 70 ml of water, to which 5 ml of 37% HCl were added. After a few minutes, a yellow precipitate formed. The suspension was stirred at room temperature for an additional 30 minutes and then stored at 4° C. overnight. The intermediate diethyl 2,4-hexadiene-5-hydroxy-1,6-dioate was collected by filtration and washed with water.

The so-obtained crude ester was heated at 100° C. with 6 ml of concentrated hydrochloric acid. The initial suspension turned into a solution when the temperature reached 60° C. After one hour, a yellow solid began to form. After 6 hours, the suspension was cooled and the pyrone acid was filtered. The volume of the filtrate was reduced by evaporation; the residual mother liquid was cooled and diethyl ether was added in order to precipitate an additional quantity of the acid, which was then recovered by filtration.

2-Pyrone-6-carboxylic acid was obtained altogether as a pale yellow solid (1.5 g, yield 31%).

Step 3—In a 100 ml three-necked round-bottom flask kept under an argon atmosphere, 5-methoxytryptamine hydrochloride (430 mg, 1.1 equiv.) was suspended in 1,2-dimethoxyethane (DME, 15 ml). Pyridine was added (0.34 ml, 2.2 equiv.) and the suspension was stirred at room temperature for 30 minutes. 2-Pyrone-6-carboxylic acid (250 mg, 1 equiv.) was then added and the internal temperature brought to 0° C. by means of an ice-bath. HOBt (1-hydroxybenxotriazole monohydrate, 260 mg, 1.1 equiv.), EDC (1-(3-dimethylaminopropyl)-3-ethylcarbodiimide hydrochloride, 370 mg, 1.1 equiv.) and triethylamine (0.34 ml, 1.4 equiv.) were then added under magnetic stirring. The mixture was stirred for an additional 15 minutes at 0° C. and subsequently allowed to react for 3 h at room temperature. The reaction course was followed by HPLC-MS. The obtained solution was concentrated under vacuum and the crude residue was purified by column chromatography, eluting with dichloromethane/methanol 98/2. N-[2-(5-methoxy-indol-3-yl)-ethyl]-2-Pyrone-6-carboxamide was recovered as a yellow solid (400 mg, 72% yield).

Experimental data for N-[2-(5-methoxy-indol-3-yl)-ethyl]-2-Pyrone-6-carboxamide

MS (ESI POS): 313 (M+H), 330 (M+H$_2$O), 376 (M+Na+CH$_3$CN)

HPLC assay: 97%

$^1$H NMR (DMSO-d$_6$, 400 MHz) δ 2.87-2.91 (m, 2H, CH$_2$CH7NH), 3.47-3.52 (m, 2H, CH$_2$CH$_2$NH), 3.75 (s, 3H, OCH$_3$), 6.55 (d, J=9.4 Hz, 1H, CH), 6.70 (dd, J$_i$=2.9 Hz, J2=8.8 Hz, 1H, aromatic H), 7.02 (br d, J=6.6 Hz, 1H, CH), 7.06 (d, J=2.1 Hz, 1H, aromatic H), 7.13 (d, J=2.2 Hz, 1H, aromatic H), 7.22 (d, J=8.8 Hz, 1H, aromatic H), 7.67 (dd, J$_1$=6.6 Hz, J$_2$=9.4 Hz, 1H, CH), 8.87 (br t, J=5.8 Hz, 1H, CH$_2$CH$_2$NH), 10.65 (br s, 1H, NH).

Biological Testing of Compounds of the Invention

Experiment 1

Potentiation of Hexobarbital-Na Sleep Time in Mice

CD1 mice were divided randomly into groups of seven mice each. The mice in each group were administered intraperitoneally a dose of one of the following: 100 mg/kg of one of test substances O-[2-(5-methoxy-indol-3-yl)-ethyl]-comenic ester, N-[2-(5-methoxyindol-3-yl)-ethyl]-commenamide, N-[2-(5-methoxy-indol-3-yl)-ethyl]-coumalylamide, N-[2-(5-methoxy-indol-3-yl)-ethyl]-chelidonamide, N-[2-(5-methoxy-indol-3-yl)-ethyl]-comanilamide or N-[2-(5-methoxy-indol-3-yl)-ethyl]-2-methoxy-commenamide in saline (0.1 ml/10 g body weight), or saline alone. Fifteen minutes later the mice received a dose of 50 mg/kg of hexobarbital-Na intravenously. Sleep time was measured in each animal as the time from loss to recovery of the righting reflex.

As shown in Table 1 below, 100 mg/kg i.p. of O-[2-(5-methoxy-indol-3-yl)-ethyl]-comenic ester, N-[2-(5-methoxy-indol-3-yl)-ethyl]-coumalylamide and N-[2-(5-methoxy-indol-3-yl)-ethyl]-commenamide significantly increased the hexobarbital-Na narcosis time and N-[2-(5-methoxy-indol-3-yl)-ethyl]-chelidonamide and N-[2-(5-methoxy-indol-3-yl)-ethyl]-comanilamide moderately increased the hexobarbital-Na narcosis time. The results demonstrate the hypnotic potency of the compounds via a GABAa positive allosteric binding mechanism.

TABLE 1

Effects of 100 mg/kg of the test compounds on the hexobarbital-Na induced sleep time in mice

| Substances | Mean Sleep Time - Vehicle (min) ± SE | Mean Sleep Time - Treatment (min) ± SE | Changes (%) vs. Vehicle | P value (t-test) |
|---|---|---|---|---|
| O-[2-(5-methoxy-indole-3-yl)-ethyl]-comenic ester | 7.28 ± 1.40 | 15.15 ± 6.02 | +108 | 0.01 |
| N-[2-(5-methoxy-indol-3-yl)-ethyl]-commenamide | 9.10 ± 2.26 | 17.13 ± 8.06 | +88 | 0.04 |
| N-[2-(5-methoxy-indole-3-yl)-ethyl]-coumalylamide | 8.02 ± 0.71 | 23.58 ± 3.19 | +194 | 0.001 |
| N-[2-(5-methoxy-indole-3-yl)-ethyl]-chelidonamide | 8.02 ± 0.71 | 12.37 ± 1.85 | +54 | 0.054 |
| N-[2-(5-methoxy-indol-3-yl)-ethyl]-comanilamide | 10.93 ± 1.30 | 17.52 ± 3.07 | +49 | 0.15 |
| N-[2-(5-methoxy-indol-3-yl)-ethyl]-2-methoxy-commenamide | 9.75 ± 1.74 | 7.70 ± 1.24 | −21 | 0.36 |

Experiment 2

$^{125}$I-Melatonin Binding in Membranes of CHO-K1 Cells

Aliquots of suspended membranes of human recombinant CHO-K1 (Chinese hamster ovary) cells stably expressing human melatonin-1 or melatonin-2 (MT-1 or MT-2) receptors or of hamster brain (MT-3) were incubated at 25° C. with 0.05 nM $^{125}$I-melatonin in buffer (25 mM HEPES, pH 7.4, 5 mM MgCl$_2$, 1 mM CaCl$_2$, 0.5% BSA) or with 0.1 nM for MT-3 alone or in the presence of 1 nM, 10 nM, 0.1 μM, 1 μM and 10 μM of test substances N-[2-(5-methoxy-indol-3-yl)-ethyl]-commenamide, N-[2-(5-methoxy-indol-3-yl)-ethyl]-comanilamide, N-[2-(5-methoxy-indol-3-yl)-ethyl]-coumalylamide, N-[2-(5-methoxy-indol-3-yl)-ethyl]-2-methoxy-commenamide, N-[2-(5-methoxy-indol-3-yl)-ethyl]-chelidonamide, O-[2-(5-methoxy-indol-3-yl)-ethyl]-comenic ester, N-[2-(5-methoxy-indol-3-yl)-ethyl]-2-Pyrone-6-carboxamide and N-[2-(2-bromo-5-methoxy-indol-3-yl)-ethyl]-coumalylamide for 3 hours for MT-1, 4 hours for MT-2 and 30 min for MT-3. The binding reaction was terminated and the membranes were washed with 4 ml of ice-cold HEPES buffer by vacuum filtration. Membranes were then collected, and the filters containing the bound $^{125}$I-melatonin were assayed for the amount of radio-activity in a ϵ-counter. Non-specific binding was evaluated using a reaction with 1 μM 6-chloromelatonin (MT-1 and MT-2) or 30 μM melatonin (MT-3).

The results, shown in Tables 2 and 3, demonstrate the competition of the compounds on specific $^{125}$I-melatonin binding to MT-1, MT-2 and MT-3 receptors. Both N-[2-(5-methoxy-indol-3-yl)-ethyl]-commenamide and N-[2-(5-methoxy-indol-3-yl)-ethyl]-comanilamide were shown to bind with a high affinity to the 3 melatonin receptor subtypes while the rest of compounds were shown to bind with at least a moderate affinity to melatonin receptors.

TABLE 2

Effects of test compounds on binding to the MT-1 or MT-2 receptors

| | MT-1 receptor binding | | | MT-2 receptor binding | | |
|---|---|---|---|---|---|---|
| | % inhibition by 10 μM | IC50 | KI | % inhibition by 10 μM | IC50 | KI |
| N-[2-5-methoxy-indol-3-yl)-ethyl]-commenamide | 99% | 24 nM | 13 nM | 101% | 13 nM | 7 nM |
| N-[2-(5-methoxy-indole-3-yl)-ethyl]-comanilamide | 98% | 42 nM | 22 nM | 100% | 65 nM | 34 nM |
| N-[2-(5-methoxy-indol-3-yl)-ethyl]-coumalylamide | 89% | 750 nM | 390 nM | 95% | 370 nM | 190 nM |
| N-[2-(5-methoxy-indole-3-yl)-ethyl]-2-methoxy-commenamide | 76% | 2130 nM | 1110 nM | 93% | 826 nM | 429 nM |
| N-[2-(5-methoxy-indol-3-yl)-ethyl]-chelidonamide | 80% | 2470 nM | 1280 nM | 89% | 1760 nM | 910 nM |
| O-[2-(5-methoxy-indol-3-yl)-ethyl]-comenic ester | 47% | na | na | 78% | 1640 nM | 850 nM |
| N-[2-(5-methoxy-indol-3-yl)-ethyl]-2-Pyrone-6-carboxamide | 50% | 10,100 nM | 5240 nM | 65% | 5060 nM | 2630 nM |
| N-[2-(2-bromo-5-methoxy-indol-3-yl)-ethyl]-coumalylamide | 76% | 2400 nM | 1250 nM | 89% | 850 nM | 441 nM |

TABLE 3

| | MT-3 receptor binding | | |
|---|---|---|---|
| | % inhibition by 10 μM | IC50 | KI |
| N-[2-5-methoxy-indol-3-yl)-ethyl]-commenamide | 98% | 800 nM | 780 nM |
| N-[2-(5-methoxy-indol-3-yl)-ethyl]-comanilamide | 100% | 310 nM | 300 nM |
| N-[2-(5-methoxy-indol-3-yl)-ethyl]-coumalylamide | 95% | 980 nM | 960 nM |
| N-[2-(5-methoxy-indol-3-yl)-ethyl]-2-methoxy-commenamide | 99% | 230 nM | 220 nM |
| N-[2-(5-methox-indol-3-yl)-ethyl]-chelidonamide | 86% | 2200 nM | 2200 nM |
| Melatonin | 100% | 47 nM | 46 nM |

0.7 nM [$^3$H] GR-113808 (5-HT$_4$) or at 37° C. 1.2 nM [$^3$H] LSD (5-HT$_{2B}$, 5-HT$_6$ and 5-HT$_7$) in buffer (50 mM Tris-HCl, pH 7.7) alone or in the presence of 1 nM, 10 nM, 0.1 μM, 1 μM, and 10 μM of N-[2-(5-methoxy-indol-3-yl)-ethyl]-commenamide, N-[2-(5-methoxy-indol-3-yl)-ethyl]-coumalylamide, N-[2-(5-methoxy-indol-3-yl)-ethyl]-comanilamide, N-[2-(5-methoxy-indol-3-yl)-ethyl]-2-methoxy-commenamide or N-[2-(5-methoxy-indol-3-yl)-ethyl]-chelidonamide for 60 minutes. The binding reaction was terminated and washed with 4 ml ice-cold 50 mM Tris-HCl buffer by vacuum filtration. Membranes were then collected, and the filters containing the bound ligands were assayed for the amount of radioactivity in a b-counter. Non-specific binding was evaluated using a reaction with 10 μM metergoline (5-HT$_{1A}$), 1 μM mianserin (5-HT$_{2A}$ and 5-HT$_{2C}$) or 10 μM serotonin (5-HT$_{1B}$, 5-HT$_{2B}$, 5-HT$_4$, 5-HT$_6$ and 5-HT$_7$).

The results, shown in Table 4 below, demonstrate the competition of the compounds on specific 5-HT receptors binding. N-[2-(5-methoxy-indol-3-yl)-ethyl]-commenamide was shown to bind with a moderate affinity to 5-HT$_{1A}$, 5-HT$_{2B}$, and 5-HT$_7$ receptors, N-[2-(5-methoxy-indol-3-yl)-ethyl]-coumalylamide was shown to bind with a moderate affinity to 5-HT$_{1B}$ and 5-HT$_7$ receptors, N-[2-(5-methoxy-indol-3-yl)-ethyl]-comanilamide was shown to bind with a moderate affinity to the 5-HT$_{1B}$ receptor, N-[2-(5-methoxy-indol-3-yl)-ethyl]-2-methoxy-commenamide was shown to bind with a moderate affinity to 5-HT$_{2B}$ and 5-HT$_7$ receptors and N-[2-(5-methoxy-indol-3-yl)-ethyl]-chelidonamide was shown to bind with a moderate affinity to 5-HT$_{1A}$, and 5-HT$_{1B}$ receptors.

TABLE 4

Effects of test compunds on binding to 5-HT receptors

| Receptor subtype | Parameter | N-[2-(5-methoxy-indole-3-yl)-ethyl]-commena-mide | N-[2-(5-methoxy-indol-3-yl)-ethyl]-coumalyla-mide | N-[2-(5-methoxy-indol-3-yl)-ethyl]-comanila-mide | N-2-(5-methoxy-indol-3-yl)-ethyl]-2-methoxy-commenamide | N-[2-(5-methoxy-indol-3-yl)-ethyl]-cheli-donamide |
|---|---|---|---|---|---|---|
| 5-HT$_{1A}$ | IC50 | 0.68 μM | 1.97 μM | 1.95 μM | 1.93 μM | 1.03 μM |
| | KI | 0.39 μM | 0.65 μM | 1.11 μM | 1.10 μM | 0.58 μM |
| 5HT$_{1B}$ | IC50 | 3.91 μM | 1.64 μM | 2.14 μM | 5.44 μM | Nt |
| | KI | 3.71 μM | 1.55 μM | 2.03 μM | 5.16 μM | Nt |
| 5-HT$_{2A}$ | IC50 | n | na | na | na | 7.5 μM |
| | KI | na | na | na | na | 2.14 μM |
| 5-HT$_{2B}$ | IC50 | 2.25 μM | 3.0 μM | 6.78 μM | 1.76 μM | 2.1 μM |
| | KI | 1.43 μM | 1.91 μM | 4.32 μM | 1.12 μM | 1.33 μM |
| 5-HT$_{2C}$ | IC50 | 7.2 μM | na | na | na | 11.2 μM |
| | KI | 3.8 μM | na | na | na | 5.8 μM |
| 5-HT$_4$ | IC50 | na | na | nt | na | nt |
| | KI | na | na | nt | na | nt |
| 5-HT$_6$ | IC50 | na | na | na | na | na |
| | KI | na | na | na | na | na |
| 5-HT$_7$ | IC50 | 0.23 μM | 0.664 μM | nt | 0.735 μM | nt |
| | KI | 0.132 μM | 0.381 μM | nt | 0.42 μM | nt |

Experiment 3

Serotonin Receptor Subtypes Binding in Membranes of CHO-K1 Cells

Aliquots of suspended membranes of human recombinant CHO-K1 cells stably expressing human 5-HT$_{1A}$, 5-HT$_{2A}$, 5-HT$_{1B}$, 5-HT$_{2B}$, 5-HT$_{2C}$, 5-HT$_4$, 5-HT$_6$ or 5-HT$_7$ receptors were pre-incubated at 25° C. with 1.5 nM [$^3$H] 8-OH-DPAT (5-HT$_{1A}$), 1.5 nM [$^3$H] Ketanserin (5-HT$_{2A}$), 0.01 nM [$^{125}$I] Cyanopindolol (5-HT$_{1B}$), 1 nM [$^3$H] Mesulergine (5-HT$_{2C}$), Experiment 4

Hypnotic compounds cause a depression of locomotor activity, reduced rearing, hypothermia, and ataxia assessed on a rotarod in mice (Crabbe et al, Psychopharmacology, 161; 408-416, 2002).

Motimeter Assay

Mice were starved for 16 hrs before treatment. Male CD1 mice, weighing 25-30 g, were treated intraperitoneally with melatonin, N-[2-(5-methoxy-indol-3-yl)-ethyl]-comanilamide or N-[2-(5-methoxy-indol-3-yl)-ethyl]-commenamide in a dose of 100 mg/kg. The horizontal (i.e. locomotion) and vertical (i.e. rearing) movements were measured for 5 minutes two times, 30 and 60 min after treatment. Eight mice/group were used. The 4-channel activity meter is a square-shaped frame containing transparent infra-red permeable acrylic cages. The frames feature two pairs of light-beam strips for measuring horizontal movements, and two pairs for measuring rearing. Each strip is equipped with 16 infra-red sensors.

On the motimeter assay melatonin, N-[2-(5-methoxy-indol-3-yl)-ethyl]-comanilamide and N-[2-(5-methoxy-indol-3-yl)-ethyl]-commenamide in the intraperitoneal dose of 100 mg/kg did not change significantly the motor activity and rearing measured between 30-35 min and 60-65 min after treatment (Table 5).

N-[2-(5-methoxy-indol-3-yl)-ethyl]-coumalylamide in the intraperitoneal dose of 100 mg/kg significantly decreased both the motor activity and rearing in the two time intervals mentioned above. These results demonstrate the hypnotic and sedative effects of N-[2-(5-methoxy-indol-3-yl)-ethyl]-coumalylamide.

Rotarod Assay

The incidences of animals running more than 120 min on the rotating rod were noted, and significances were calculated by non-parametric $x^2$ test. 8 mice/group were used.

The rotarod apparatus is divided into five test zones, so that up to five mice may be tested at the same time. The rod has been specially machined to provide a suitable grip for the animal. The diameter of the rod is 3.5 cm. The rotation speed was 15 rpm. When the animal falls off the rotating rod, it presses a button to record automatically the time spent on the rod. On the day before the experiment the mice were trained to run on the rod rotating with 15 rpm. Diazepam was administered orally 60 min before the rotarod assay, test substances were administered intraperitoneally 15 min before testing.

On the rotarod test both N-[2-(5-methoxy-indol-3-yl)-ethyl]-comanilamide and N-[2-(5-methoxy-indol-3-yl)-ethyl]-commenamide dose dependently impaired the performance of mice at 15 rpm rotation speed (Table 6).

Diazepam in the oral dose of 1.5 mg/kg significantly potentiated the rotarod performance impairing effects of both compounds in all the three doses applied. These results demonstrate the synergistic hypnotic effects of N-[2-(5-methoxy-indol-3-yl)-ethyl]-comanilamide and N-[2-(5-methoxy-indol-3-yl)-ethyl]-commenamide administered with the benzodiazepine hypnotic agent diazepam.

TABLE 5

Effects of melatonin and N-[2-(5-methoxy-indol-3-yl)-ethyl]-coumalylamide on motor activity in mice (horizontal movement)

| Substances | Dose mg/kg | 30 min Means ± SE | 60 min Means ± SE |
|---|---|---|---|
| Vehicle | — | 430.0 ± 30.1 | 316.4 ± 35.1 |
| Melatonin changes (%) | 100 i.p. | 316.1 ± 45.5 −26.5 | 256.1 ± 27.3 −19.0 |
| N-[2-(t-methoxy-indol-3-yl)-ethyl]-coumalylamide Changes (%) | 100 i.p. | 158.8 ± 37.0* −63.1 | 62.3 ± 16.6* −80.3 |

TABLE 6

Effects of the interaction of N-[2-(5-methoxy-indol-3-yl)-ethyl]-comanilamide and N-[2-(5-methoxy-indol-3-yl)-ethyl]-commenamide with Diazepam on rotarod assay in mice

| Substances Doses mg/k | Incidence of performance |
|---|---|
| Vehicle p.o. + Vehicle i.p. | 8/8 |
| Diazepan 1.5 p.o. + Vehicle i.p. | 6/8 |
| Vehicle p.o. + N-[2-(5-methoxy-indole-3-yl)ethyl-comanilamide 5 i.p. | 6/8 |
| Vehicle p.o. + N-[2-(5-methoxy-indol-3-yl)-ethyl]-comanilamide 20 i.p. | 5/8 |
| Vehicle p.o. + N-[2-(5-methoxy-indol-3-yl)-ethyl]-comanilamide 50 i.p. | 5/8 |
| Vehicle p.o. + N-[2-(5-methoxy-indol-3-yl)-ethyl]-commenamide 5 i.p. | 8/8 |
| Vehicle p.o. + N-[2-(5-methoxy-indol-3-yl)-ethyl]-commenamide 20 i.p. | 5/8 |
| Vehicle p.o. + N-[2-(5-methoxy-indol-3-yl)-ethyl]-commenamide 50 i.p. | 5/8 |
| Diazepam 1.5 p.o. + N-[2-(5-methoxy-indol-3-yl)-ethyl]-comanilamide 5 i.p. | 4/8* |
| Diazepam 1.5 p.o. + N-[2-(5-methoxy-indol-3-yl)-ethyl]-comanilamide 20 i.p. | 2/8*** |
| Diazepam 1.5 p.o. + N-[2-(5-methoxy-indol-3-yl)-ethyl]-comanilamide 50 i.p. | 1/8*** |
| Diazepam 1.5 p.o. + N-[2-(5-methoxy-indol-3-yl)-ethyl]-commenamide 5 i.p. | 5/8 |
| Diazepam 1.5 p.o. + N-[2-(5-methoxy-indol-3-yl)-ethyl]-commenamide 20 i.p. | 3/8** |
| Diazepam 1.5 p.o. + N-[2-(5-methoxy-indol-3-yl)-ethyl]-commenamide 50 i.p. | 1/8*** |

*$p < 0.05$
**$p < 0.01$
***$p < 0.005$
****$p < 0.0001$

Experiment 5

Adipocytes were glucose-starved for 1 h in Hepes-salt buffer containing 2% FFA-free BSA. FFA (free fatty acids) were then added to the cells at the indicated concentrations (300 μM) for the indicated times (3 h). 10 min before the end of the FFA treatment, the cells were stimulated with insulin (20 nM)/melatonin (10 nM)/test compounds (10 nM) at 37° C. 2-[$^3$H]-deoxy-d-glucose at 1 μCi/mL and 0.1 mM unlabeled 2-deoxyglucose in KRP-HEPES buffer was added and cells were incubated for 10 min at room temperature. Non-specific glucose uptake was measured by parallel incubations in the presence of 10 μM cytochalasin B, which blocks transporter-mediated glucose uptake, and was subtracted from total uptake in each assay. Cells were then washed three times with ice-cold phosphate buffered saline (PBS) and solubilized in 1M NaOH for 20 minutes. The sample was then counted using a scintillation counter. 2-[$^3$H]-deoxy-d-glucose uptake was assayed in triplicates for each condition in at least 3 independent experiments. 2-[$^3$H]-deoxy-d-glucose uptake (counts per minute-cpm) are presented as mean±SE of triplicates in a representative experiment or results of three independent experiments. ANOVA test was used with significance of $P<0.05$ (Table 7).

TABLE 7

| Substances | 2-[$^3$H]-deoxy-d-glucose uptake (cpm) | S.E. | P value |
|---|---|---|---|
| Non specific uptake | 709 | 29.4 | |
| Insulin (20 nM) | 1839 | 163.2 | d |
| FFA (300 μM) | 975 | 44.5 | |
| Insulin + FFA (20 nM and 300 μM) | 1212 | 69.6 | a |
| Insulin + FFA + Melatonin (10 nM) | 1489 | 32.3 | ab |
| Insulin + FFA + N-[2-(5-methoxy-indol-3-yl)-ethyl]-commenamide (10 nM) | 1530 | 80.6 | abc |
| Insulin + FFA + N-[2-(5-methoxy-indol-3-yl)-ethyl]-comanilamide (10 nM) | 1492 | 37.5 | ab |
| Insulin + FFA + N-[2-(5-methoxy-indol-3-yl)-ethyl]-coumalylamide (10 nM) | 1494 | 134.9 | ab |
| Insulin + FFA + N-[2-(5-methoxy-indol-3-yl)-ethyl]-2-methoxy-commenamide (10 nM) | 1522 | 35.7 | ab |
| Insulin + FFA + N-[2-(5-ethoxy-indol-3-yl)-ethyl]-chelidonamide (10 nM) | 1407 | 34.4 | ab |
| Insulin + FFA + O-[2-(5-methoxy-indol-3-yl)-ethyl]-comenic ester (10 nM) | 1787 | 118.7 | abc |

(a: P < 0.05 vs C group, b: P < 0.05 vs D group, c: P < 0.05 vs melatonin group, d: P < 0.05 vs all other groups, ANOVA)

3T3-L1 adipocytes were used as an in vitro model to assess the cellular effect of pyrone-indole derivatives and melatonin on insulin resistance initiated by high FFA treatment. In 3T3-L1 adipocytes FFA treatment impaired insulin signaling and melatonin/pyrone-indole derivatives improved glucose transport. Therefore, melatonin and pyrone-indole derivatives could ameliorate insulin resistance initiated by FFA.

We claim:

1. A compound having the formula:

Ar—B—Ar'  (I)

wherein:
—B— represents:
—X—Y-Z-
wherein
X represents —(CH$_2$)$_n$ (wherein n is 0-6);
Y represents oxygen, sulphur, or >NH;
Z represents >C=O, >O or >COO;
wherein at least one of X, Y and Z must be present;
Ar represents an indole nucleus ring system:

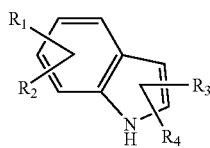

Ar' represents an alpha-, beta- or gamma-pyrone nucleus ring system:

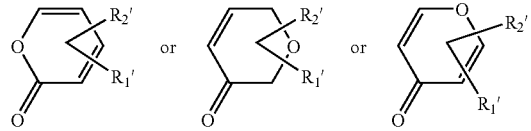

wherein each of R$_{1-4}$ substitutes the ring system Ar at any available position (including the N-position) and each of R$_{1'}$-R$_{2'}$ substitutes the ring system Ar' at any available position and wherein each of R$_{1-4}$ and R$_{1'-2'}$ independently represents hydrogen, oxygen, halo, halo-C$_{1-5}$ alkyl, aryl, acyl, a C$_{5-7}$ heterocyclic group containing 1-3 hetero atoms independently selected from nitrogen, oxygen or sulphur; a C$_{6-8}$ heteroaryl group containing 1-3 hetero atoms independently selected from nitrogen, oxygen or sulphur, C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{1-5}$ alkynyl, hydroxy-C$_{1-5}$ alkyl, nitro, amino, cyano, cyanamido, guanidino, amidino, acylamido, C$_{1-5}$ alkylamine, C$_{1-5}$ alkylamido, hydroxy, thiol, acyloxy, azido, C$_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-C$_{1-5}$ alkyl, aryl, a C$_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{2-5}$ alkynyl, hydroxy-C$_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;
and either of R$_3$ or R$_4$ further can include or represent a bond to B;
wherein Ar can be bonded to B at any position on the 5-membered ring portion of the Ar ring, including the N-position, and Ar' can be bonded to B at any carbon on the Ar' ring not substituted by R$_{1'}$ and R$_{2'}$;
or a pharmaceutically acceptable salt or stereoisomer thereof.

2. A compound of claim 1, wherein X is —(CH$_2$)$_n$, wherein n is 0-6, Y is >NH or >O and Z is >CO.

3. A compound of claim 2, wherein Ar' is an alpha-pyrone ring system.

4. A compound of claim 2, wherein Ar' is a beta-pyrone ring system.

5. A compound of claim 2, wherein Ar' is a gamma-pyrone ring system.

6. A compound of claim 1, wherein
X is —(CH$_2$)$_2$—, Y is >NH or >O, and Z is >CO,
Ar is an indole ring; R$_3$ is a bond to X on position 3 of the indole ring; R$_1$ is a methoxy group on position 5 of the indole ring, and each of R$_2$ and R$_4$ is hydrogen;
Ar' is a gamma-pyrone ring bonded to Z at position 2 of the pyrone ring; R$_{1'}$ is hydrogen or a hydroxy group on position 5 of the pyrone ring; and R$_{2'}$ is hydrogen or a carboxy group on position 6 of the gamma-pyrone ring;
or a pharmaceutically acceptable salt or stereoisomer thereof.

7. A compound of claim 1, wherein
X is —(CH$_2$)$_2$—, Y is >NH or >O and Z is >CO;
Ar is an indole ring; R$_3$ is a bond to X on position 3 of the indole ring; R$_1$ is a methoxy group at position 5 of the indole ring and each of R$_2$ and R$_4$ is hydrogen;
Ar' is an alpha-pyrone ring substituted by Z at position 5 of the pyrone ring; and R$_{1'}$ and R$_{2'}$ are each hydrogen;
or a pharmaceutically acceptable salt or stereoisomer thereof.

8. A compound of claim 1, wherein
X is —(CH$_2$)$_2$—, Y is >NH; and Z is >CO;
Ar is an indole ring; R$_3$ is a bond to X on position 3 of the indole ring; R$_1$ is a methoxy group at position 5 of the indole ring, and each of R$_2$ and R$_4$ is H;
Ar' is a gamma-pyrone ring substituted by Z at position 2 of the pyrone ring; R$_{1'}$ is a hydroxy group at position 5 of the pyrone ring; and R$_{2'}$ is hydrogen;
or a salt or stereoisomer thereof.

9. A compound of claim 1, wherein
X is —(CH$_2$)$_2$—, Y is >O, and Z is >CO;
Ar is an indole ring; R$_3$ is a bond to X at position 3 of the indole ring; R$_1$ is a methoxy group at position 5 of the indole ring, and each of R$_2$ and R$_4$ is H;
Ar' is a gamma-pyrone ring substituted by Z at position 2 of the pyrone ring; R$_{1'}$ is a hydroxy group at position 5 of the pyrone ring; and R$_{2'}$ is hydrogen;
or a salt or stereoisomer thereof.

10. A compound of claim 1, wherein
X is —(CH$_2$)$_2$—, Y is >NH, and Z is >CO;
Ar is an indole ring; R$_3$ is a bond to X at position 3 of the indole ring; R$_1$ is a methoxy group at position 5 of the indole ring, and each of R$_2$ and R$_4$ is hydrogen;
Ar' is a gamma-pyrone ring substituted by Z at position 2 of the pyrone ring; R$_{1'}$ and R$_{2'}$ are each hydrogen;
or a salt or stereoisomer thereof.

11. A compound of claim 1, wherein
X is —(CH$_2$)$_2$—, Y is >NH and Z is >CO;
Ar is an indole ring; R$_3$ is a bond to X at position 3 of the indole ring; R$_1$ is a methoxy group at position 5 of the indole ring, and each of R$_2$ and R$_4$ is H;
Ar' is an alpha-pyrone ring substituted by Z at position 5 of the pyrone ring; and R$_{1'}$ and R$_{2'}$ are hydrogen;
or a salt or stereoisomer thereof.

12. A pharmaceutical formulation comprising a therapeutically effective amount of a compound having the formula:

wherein:
—B— represents:
—X—Y-Z- wherein
X represents —(CH$_2$)$_n$ (wherein n is 0-6);
Y represents oxygen, sulphur, >NH or is absent;
Z represents >C=O, >O or >COO or is absent;
wherein at least one of X, Y and Z must be present;
Ar represents an indole nucleus ring system:

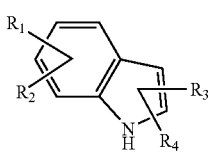

Ar' represents an alpha-, beta- or gamma-pyrone nucleus ring system:

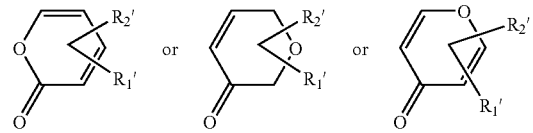

wherein each of R$_{1-4}$ substitutes the ring system Ar at any available position (including the N-position) and each of R$_{1'}$-R$_{2'}$ substitutes the ring system Ar' at any available position and wherein each of R$_{1-4}$ and R$_{1'-2'}$ independently represents hydrogen, oxygen, halo, halo-C$_{1-5}$ alkyl, aryl, acyl, a C$_{5-7}$ heterocyclic group containing 1-3 hetero atoms independently selected from nitrogen, oxygen or sulphur; a C$_{6-8}$ heteroaryl group containing 1-3 hetero atoms independently selected from nitrogen, oxygen or sulphur, C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{1-5}$ alkynyl, hydroxy-C$_{1-5}$ alkyl, nitro, amino, cyano, cyanamido, guanidino, amidino, acylamido, C$_{1-5}$ alkylamine, C$_{1-5}$ alkylamido, hydroxy, thiol, acyloxy, azido, C$_{1-5}$ alkoxy, carboxy, carbonylamido or styryl; wherein said arylalkyl, arylalkenyl, aralkynyl, or styryl group optionally can be ring-substituted by one to four substituents independently selected from the group consisting of hydrogen, halo, halo-C$_{1-5}$ alkyl, aryl, a C$_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{2-5}$ alkynyl, hydroxy-C$_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of R$_3$ or R$_4$ further can include or represent a bond to B;

wherein Ar can be bonded to B at any position on the five-membered ring portion of the Ar ring, including the N-position, and Ar' can be bonded to B at any carbon on the Ar' ring not substituted by R$_{1'}$ and R$_{2'}$; or a salt or stereoisomer thereof; in combination with one or more pharmaceutically acceptable diluents, preservatives, solubilizers, emulsifiers, adjuvants, excipients or carriers.

13. A pharmaceutical formulation according to claim 12, which is characterized by at least one of the following features:

(i) it is adapted for oral, rectal, parenteral, nasal, vaginal, sublingual or topical administration;

(ii) it is in unit dosage form, each unit dosage comprising an amount of at least one compound, salt or stereoisomer of claim 12 which is within the range of about 2.5 µg-about 25 mg/kg;

(iii) it is an extended release formulation, wherein at least one compound of claim 12 is released at a predetermined controlled rate.

14. A pharmaceutical formulation according to claim 13, which is adapted for oral administration and is in unit dosage form, wherein each unit dosage form comprises an amount of said at least one compound, salt or stereoisomer within the range of about 0.2 mg-about 500 mg.

15. A pharmaceutical formulation according to claim 14, which is adapted for oral administration and is in unit dosage form, wherein each unit dosage form comprises an amount of said at least one compound, salt or stereoisomer within the range of about 0.5 mg-about 50 mg.

16. A pharmaceutical formulation according to claim 14, wherein each unit dosage form comprises an amount of said at least one compound, salt or stereoisomer within the range of about 2.5 mg-about 20 mg.

17. A pharmaceutical formulation according to claim 13, which is adapted for parenteral or topical administration and is in unit dosage form, wherein each unit dosage form comprises an amount of said at least one compound, salt or stereoisomer within the range of about 2.5 µg-about 5 mg/kg.

18. A pharmaceutical formulation according to claim 13, which is adapted for parenteral or topical administration and is in unit dosage form, wherein each unit dosage form comprises an amount of said at least one compound, salt or stereoisomer within the range of about 100 µg-about 100 mg.

19. A pharmaceutical formulation according to claim 12 wherein said formulation is in unit dosage form, and wherein said unit dosage form provides an amount of said at least one compound, salt or stereoisomer effective for treating type II diabetes, depression, anxiety, sleep disorders, glaucoma, or opiate tolerance or withdrawal symptoms; or for enhancing cognition or for inducing anesthesia.

20. The pharmaceutical formulation according to claim 12, wherein said formulation is in unit dosage form, wherein said unit dosage form provides an amount of said compound, salt or stereoisomer effective for treating a chronobiological-based disorder, a circadian sleep disorder, diabetes stabilization or weight gain disorder.

21. The pharmaceutical formulation according to claim 12, wherein said formulation is in unit dosage form which provides an amount of a compound of claim 12 or a salt or stereoisomer thereof effective for treating a sleep disorder or sleep disturbance or for improving sleep quality or for altering a circadian rhythm.

22. The pharmaceutical formulation of claim 21, which further comprises a sedative, hypnotic, anxiolytic, antipsychotic, antianxiety agent, tranquilizer, melatonin agonist or antagonist, melatonin, benzodiazepine, barbiturate, or 5HT-2 antagonist.

23. The pharmaceutical formulation according to claim 12, wherein said formulation is in unit dosage form which provides an amount of a compound of claim 12 or a salt or stereoisomer thereof effective for treating diabetes.

24. The pharmaceutical formulation of claim 23, which further comprises an antidiabetic agent.

25. A method for treating diabetes type II, depression, anxiety, sleep disorder, glaucoma, or opiate tolerance or withdrawal symptoms; or for enhancing cognition which comprises administering to an animal or human in need thereof an effective amount of a pharmaceutical formulation comprising an effective amount of a compound having the formula Ar—B—Ar'     (I)

wherein:
—B— represents:
—X—Y-Z- wherein
X represents —(CH$_2$)$_n$ (wherein n is 0-6),
Y represents oxygen, sulphur, >NH or is absent;
Z represents >C=O, >O or >COO or is absent;
wherein at least one of X, Y and Z must be present;
Ar represents an indole nucleus ring system:

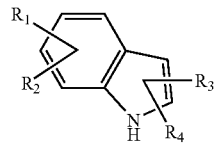

Ar' represents an alpha-, beta- or gamma-pyrone nucleus ring system:

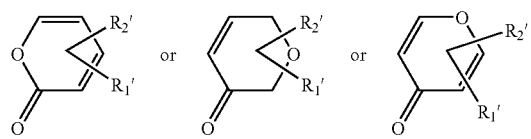

wherein each of R$_{1-4}$ substitutes the ring system Ar at any available position (including the N-position) and each of R$_{1'}$-R$_{2'}$ substitutes the ring system Ar' at any available position and wherein each of R$_{1-4}$ and R$_{1'-2'}$ independently represents hydrogen, oxygen, halo, halo-C$_{1-5}$ alkyl, aryl, acyl, a C$_{5-7}$ heterocyclic group containing 1-3 hetero atoms independently selected from nitrogen, oxygen or sulphur; a C$_{6-8}$ heteroaryl group containing 1-3 hetero atoms independently selected from nitrogen, oxygen or sulphur, C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{1-5}$ alkynyl, hydroxy-C$_{1-5}$ alkyl, nitro, amino, cyano, cyanamido, guanidino, amidino, acylamido, C$_{1-5}$ alkylamine, C$_{1-5}$ alkylamido, hydroxy, thiol, acyloxy, azido, C$_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-C$_{1-5}$ alkyl, aryl, a C$_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{2-5}$ alkynyl, hydroxy-C$_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of R$_3$ or R$_4$ further can include or represent a bond to B;

wherein Ar can be bonded to B at any position on the five-membered ring portion of the Ar ring, including the N-position, and Ar' can be bonded to B at any carbon on the Ar' ring not substituted by R$_{1'}$ and R$_{2'}$; or a salt or stereoisomer thereof.

26. A method for treating a chronobiological-based disorder, a circadian sleep disorder, diabetes stabilization or weight gain disorder; which comprises administering to an animal or human in need of such treatment a formulation comprising an effective amount of a compound having the formula

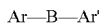 (I)

wherein:
—B— represents:
—X—Y-Z-
wherein
X represents —(CH$_2$)$_n$ (wherein n is 0-6),
Y represents oxygen, sulphur, >NH or is absent;
Z represents >C=O, >O or >COO or is absent;
wherein at least one of X, Y and Z must be present;
Ar represents an indole nucleus ring system:

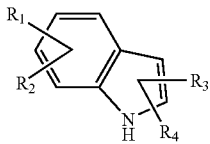

Ar' represents an alpha-, beta- or gamma-pyrone nucleus ring system:

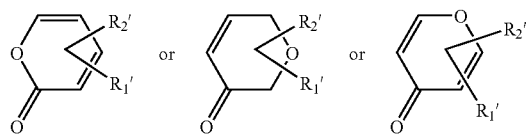

wherein each of R$_{1-4}$ substitutes the ring system Ar at any available position (including the N-position) and each of R$_{1'}$-R$_{2'}$ substitutes the ring system Ar' at any available position and wherein each of R$_{1-4}$ and R$_{1'-2'}$ independently represents hydrogen, oxygen, halo, halo-C$_{1-5}$ alkyl, aryl, acyl, a C$_{5-7}$ heterocyclic group containing 1-3 hetero atoms independently selected from nitrogen, oxygen or sulphur; a C$_{6-8}$ heteroaryl group containing 1-3 hetero atoms independently selected from nitrogen, oxygen or sulphur, C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{1-5}$ alkynyl, hydroxy-C$_{1-5}$ alkyl, nitro, amino, cyano, cyanamido, guanidino, amidino, acylamido, C$_{1-5}$ alkylamine, C$_{1-5}$ alkylamido, hydroxy, thiol, acyloxy, azido, C$_{1-5}$ alkoxy, carboxy, carbonylamido or styryl; wherein said arylalkyl, arylalkenyl, aralkynyl, or styryl group optionally can be ring-substituted by one to four substituents independently selected from the group consisting of hydrogen, halo, halo-C$_{1-5}$ alkyl, aryl, a C$_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{2-5}$ alkynyl, hydroxy-C$_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;
and either of R$_3$ or R$_4$ further can include or represent a bond to B;
wherein Ar can be bonded to B at any position on the five-membered ring portion of the Ar ring, including the N-position, and Ar' can be bonded to B at any carbon on the Ar' ring not substituted by R$_{1'}$ and R$_{2'}$; or a salt or stereoisomer thereof.

27. A method for altering a circadian rhythm, for improving sleep quality or for treating a sleep disorder or sleep disturbance in a human or animal in need thereof which comprises administering to said human or animal a formulation comprising an effective amount of a compound, having the formula

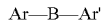 (I)

wherein:
—B— represents:
—X—Y-Z- wherein
X represents —(CH$_2$)$_n$ (wherein n is 0-6),
Y represents oxygen, sulphur, >NH or is absent;
Z represents >C=O, >O or >COO or is absent;
wherein at least one of X, Y and Z must be present;
Ar represents an indole nucleus ring system:

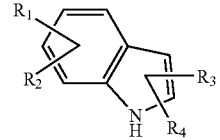

Ar' represents an alpha-, beta- or gamma-pyrone nucleus ring system:

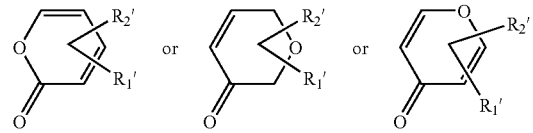

wherein each of R$_{1-4}$ substitutes the ring system Ar at any available position (including the N-position) and each of R$_{1'}$-R$_{2'}$ substitutes the ring system Ar' at any available position and wherein each of R$_{1-4}$ and R$_{1'-2'}$ independently represents hydrogen, oxygen, halo, halo-C$_{1-5}$ alkyl, aryl, acyl, a C$_{5-7}$ heterocyclic group containing 1-3 hetero atoms independently selected from nitrogen, oxygen or sulphur; a C$_{6-8}$ heteroaryl group containing 1-3 hetero atoms independently selected from nitrogen, oxygen or sulphur, C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{1-5}$ alkynyl, hydroxy-C$_{1-5}$ alkyl, nitro, amino, cyano, cyanamido, guanidino, amidino, acylamido, C$_{1-5}$ alkylamine, C$_{1-5}$ alkylamido, hydroxy, thiol, acyloxy, azido, C$_{1-5}$ alkoxy, carboxy, carbonylamido or styryl; wherein said arylalkyl, arylalkenyl, aralkynyl, or styryl group optionally can be ring-substituted by one to four substituents independently selected from the group consisting of hydrogen, halo, halo-C$_{1-5}$ alkyl, aryl, a C$_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; C$_{1-5}$ alkyl, C$_{2-5}$ alkenyl, C$_{2-5}$ alkynyl, aryl-C$_{1-5}$ alkyl, aryl-C$_{2-5}$ alkenyl, aryl-C$_{2-5}$ alkynyl, hydroxy-C$_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;
and either of R$_3$ or R$_4$ further can include or represent a bond to B;
wherein Ar can be bonded to B at any position on the five-membered ring portion of the Ar ring, including the N-position, and Ar' can be bonded to B at any carbon on the Ar' ring not substituted by $R_{1'}$ and $R_{2'}$; or a salt or stereoisomer thereof.

28. The method of claim 27, wherein said formulation is administered in combination with an agent known to be useful for enhancing sleep quality or treating a sleep disorder or sleep disturbance.

29. The method of claim 28, wherein said agent comprises a sedative, hypnotic, anxiolytic, anti-psychotic, anti-anxiety agent, tranquilizer, melatonin agonist or antagonist, melatonin, benzodiazepine, barbiturate or 5HT-2 antagonist.

30. The method of claim 27, which is administered in combination with light therapy.

31. A method for treating diabetes in a human in need thereof which comprises administering to said human a formulation comprising an effective amount of a compound having the formula Ar—B—Ar'  (I)

wherein:
—B— represents:
—X—Y-Z-
wherein
X represents —(CH$_2$)$_n$ (wherein n is 0-6), in which the alkyl moiety is linear;
Y represents oxygen, sulphur, >NH or is absent;
Z represents >C=O, >O or >COO or is absent;
wherein at least one of X, Y and Z must be present;
Ar represents an indole nucleus ring system:

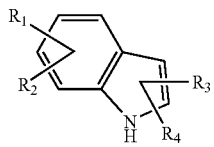

Ar' represents an alpha-, beta- or gamma-pyrone nucleus ring system:

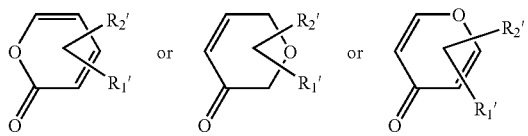

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five-membered ring portion of the Ar ring, including the N-position, and Ar' can be bonded to B at any carbon on the Ar' ring not substituted by $R_{1'}$ and $R_{2'}$; or a salt or stereoisomer thereof.

32. The method of claim 31, wherein said formulation is administered in combination with a known anti-diabetes agent.

33. The method of claim 25, wherein said formulation is in a form suitable for oral, parenteral, nasal, vaginal, rectal, sublingual or topical administration.

34. The method of claim 26, wherein said formulation is in a form suitable for oral, parenteral, nasal, vaginal, rectal, sublingual or topical administration.

35. The method of claim 25, wherein said formulation is in an extended release oral dosage form.

36. The method of claim 26, wherein said formulation is in an extended release oral dosage form.

37. A compound having the formula:

Ar—B—Ar'  (I)

wherein:
—B— represents:
—X—Y-Z-
wherein
X represents —(CH$_2$)$_n$ (wherein n is 0-6);
Y represents oxygen, sulphur, or >NH;
Z represents >C=O, >O, >COO or is absent;
wherein at least one of X, Y and Z must be present;
Ar represents an indole nucleus ring system:

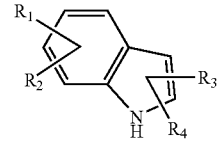

Ar' represents an alpha- or beta-pyrone nucleus ring system:

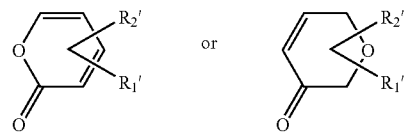

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five-membered ring portion of the Ar ring including the N-position, and Ar' can be bonded to B at any carbon on the Ar' ring not substituted by $R_{1'}$ and $R_{2'}$;

or a pharmaceutically acceptable salt or stereoisomer thereof.

38. A compound having the formula:

Ar—B—Ar'  (I)

wherein:

—B— represents:

—X—Y-Z- wherein

X represents —(CH$_2$)$_n$ (wherein n is 0-6);

Y represents oxygen or sulphur;

Z represents >C=O, >O, >COO or is absent;

wherein at least one of X, Y and Z must be present;

Ar represents an indole nucleus ring system:

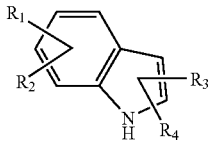

Ar' represents and alpha-, beta- or gamma-pyrone nucleus ring system:

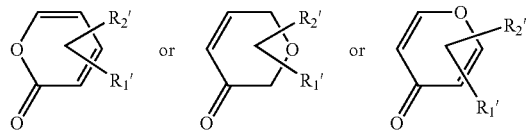

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five-membered ring portion of the Ar ring including the N-position, and Ar' can be bonded to B at any carbon on the Ar' ring not substituted by $R_{1'}$ and $R_{2'}$;

or a pharmaceutically acceptable salt or stereoisomer thereof.

39. A compound having the formula:

Ar—B—Ar'  (I)

wherein:

—B— represents:

—X—Y-Z- wherein

X represents —(CH$_2$)$_n$ (wherein n is 0-6);

Y represents oxygen, sulphur, >NH or is absent;

Z represents >C=O, >O or >COO;

wherein at least one of X, Y and Z must be present;

Ar represents an indole nucleus ring system:

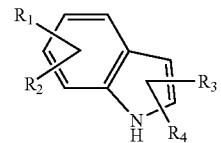

Ar' represents a beta- or gamma-pyrone nucleus ring system:

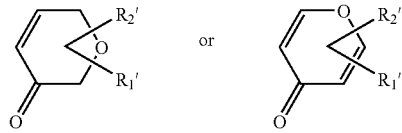

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said aryalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five-membered ring portion of the Ar ring including the N-position, and Ar' can be bonded to B at any carbon on the Ar' ring not substituted by $R_{1'}$ and $R_{2'}$;

or a pharmaceutically acceptable salt or stereoisomer thereof.

40. A compound having the formula:

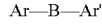  (I)

wherein:
—B— represents:
—X—Y-Z-
wherein
X represents —$(CH_2)_n$ (wherein n is 0-6);
Y represents oxygen, sulphur, or >NH or is absent;
Z represents >C=O, >O, >COO or is absent;
wherein at least one of X, Y and Z must be present;
Ar represents an indole nucleus ring system:

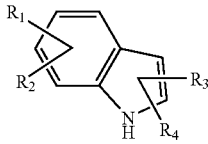

Ar' represents a beta-pyrone nucleus ring system:

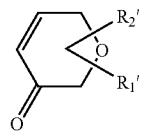

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said aryalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five membered ring portion of the Ar ring including the N-position, and Ar' can be bonded to B at any carbon on the Ar' ring not substituted by $R_{1'}$ and $R_{2'}$;

or a pharmaceutically acceptable salt or stereoisomer thereof.

41. A compound having the formula:

  (I)

wherein:
—B— represents:
—X—Y-Z-
wherein
X represents —$(CH_2)_n$ (wherein n is 0-6);
Y represents oxygen, sulphur or is absent;
Z represents >C=O, >O, >COO or is absent;
wherein at least one of X, Y and Z must be present;
Ar represents an indole nucleus ring system:

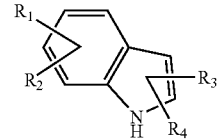

Ar' represents a beta- or gamma-pyrone nucleus ring system:

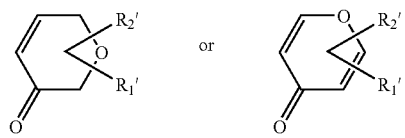

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five-membered ring portion of the Ar ring including the N-position, and Ar' can be bonded to B at any carbon on the Ar' ring not substituted by $R_{1'}$ and $R_{2'}$;

or a pharmaceutically acceptable salt or stereoisomer thereof.

42. A pharmaceutical formulation comprising a therapeutically effective amount of a compound having the formula:

$$Ar\text{—}B\text{—}Ar' \quad (I)$$

wherein:
—B— represents:
—X—Y-Z-
wherein
X represents —$(CH_2)_n$ (wherein n is 0-6)
Y represents oxygen, sulphur, >NH or is absent;
Z represents >C=O, >O or >COO or is absent;
wherein at least one of X, Y and Z must be present;
Ar represents an indole nucleus ring system:

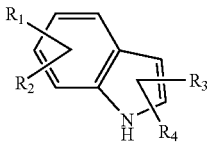

Ar' represents a beta- or gamma-pyrone nucleus ring system:

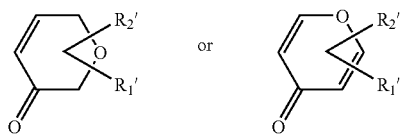

wherein each of $R_{1-4}$ substitutes the ring system Ar at any available position (including the N-position) and each of $R_{1'}$-$R_{2'}$ substitutes the ring system Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen or sulphur; a $C_{6-8}$ heteroaryl group containing 1-3 hetero atoms independently selected from nitrogen, oxygen or sulphur, $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{1-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen and sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the five-membered ring portion of the Ar ring including the N-position, and Ar' can be bonded to B at any carbon on the Ar' ring not substituted by $R_{1'}$ and $R_{2'}$; or a salt or stereoisomer thereof; in combination with one or more pharmaceutically acceptable diluents, preservatives, solubilizers, emulsifiers, adjuvants, excipients or carriers.

43. A compound of claim 1, 37, 38, 39, 40 or 41, wherein Ar is bonded to B at the 3-position of Ar.

44. A compound of claim 1, 37, 38, 39, 40 or 41, wherein Ar is bonded to B at the N-position of Ar.

45. A pharmaceutical formulation according to claim 42, which is characterized by at least one of the following features:

(i) it is adapted for oral, rectal, parenteral, nasal, vaginal, sublingual or topical administration;

(ii) it is in unit dosage form, each unit dosage comprising an amount of at least one compound, salt or stereoisomer of claim 42 which is within the range of about 2.5 μg-about 25 mg/kg;

(iii) it is an extended release formulation, wherein at least one compound of claim 42 is released at a predetermined controlled rate.

46. A pharmaceutical formulation according to claim 45, which is adapted for oral administration and is in unit dosage form, wherein each unit dosage form comprises an amount of said at least one compound, salt or stereoisomer within the range of about 0.2 mg-about 500 mg.

47. A pharmaceutical formulation according to claim 46, wherein each unit dosage form comprises an amount of said at least one compound, salt or stereoisomer within the range of about 0.5 mg-about 50 mg.

48. A pharmaceutical formulation according to claim 46, wherein each unit dosage form comprises an amount of said at least one compound, salt or stereoisomer within the range of about 2.5 mg-about 20 mg.

49. A pharmaceutical formulation according to claim 45, which is adapted for parenteral or topical administration and is in unit dosage form, wherein each unit dosage form comprises an amount of said at least one compound, salt or stereoisomer within the range of about 2.5 μg-about 5 mg/kg.

50. A pharmaceutical formulation according to claim 45, which is adapted for parenteral or topical administration and is in unit dosage form, wherein each unit dosage form comprises an amount of said at least one compound, salt or stereoisomer within the range of about 100 μg-about 100 mg.

51. A pharmaceutical formulation according to claim 42, wherein said formulation is in unit dosage form, and wherein said unit dosage form provides an amount of at least one compound, salt or stereoisomer effective for treating type II diabetes, depression, anxiety, sleep disorders, glaucoma, or opiate tolerance or withdrawal symptoms; or for enhancing cognition or for inducing anesthesia.

52. The pharmaceutical formulation according to claim 42, wherein said formulation is in unit dosage form, wherein said unit dosage form provides an amount of compound, salt or stereoisomer effective for treating a chronobiological-based disorder, a circadian sleep disorder, diabetes stabilization or weight gain disorder.

53. The pharmaceutical formulation according to claim 42, wherein said formulation is in unit dosage form which provides an amount of a compound of claim 42 or a salt or stereoisomer thereof effective for treating a sleep disorder or sleep disturbance or for improving sleep quality or for altering a circadian rhythm.

54. The pharmaceutical formulation of claim 53, which further comprises a sedative, hypnotic, anxiolytic, antipsychotic, antianxiety agent, tranquilizer, melatonin agonist or antagonist, melatonin, benzodiazepine, barbiturate, or 5HT-2 antagonist.

55. The pharmaceutical formulation according to claim 42, wherein said formulation is in unit dosage form which provides an amount of a compound of claim 42 or a salt or stereoisomer thereof effective for treating diabetes.

56. The pharmaceutical formulation of claim 55, which further comprises an antidiabetic agent.

\* \* \* \* \*